(12) United States Patent
Dvorak et al.

(10) Patent No.: US 10,543,108 B2
(45) Date of Patent: Jan. 28, 2020

(54) SPINAL IMPLANT SYSTEM AND METHOD

(71) Applicant: Warsaw Orthopedic, Inc., Warsaw, IN (US)

(72) Inventors: Marcel F. Dvorak, Vancouver (CA); Charles G. Fisher, Vancouver (CA)

(73) Assignee: Warsaw Orthopedic, Inc., Warsaw, IN (US)

( * ) Notice: Subject to any disclaimer, the term of this patent is extended or adjusted under 35 U.S.C. 154(b) by 0 days.

(21) Appl. No.: 15/807,646

(22) Filed: Nov. 9, 2017

(65) Prior Publication Data
US 2018/0064559 A1 Mar. 8, 2018

Related U.S. Application Data

(62) Division of application No. 14/835,951, filed on Aug. 26, 2015, now Pat. No. 9,877,846.

(60) Provisional application No. 62/105,579, filed on Jan. 20, 2015.

(51) Int. Cl.
| | |
|---|---|
| *A61F 2/46* | (2006.01) |
| *A61F 2/44* | (2006.01) |
| *A61B 17/16* | (2006.01) |
| *A61B 17/70* | (2006.01) |
| *A61B 90/00* | (2016.01) |
| *A61F 2/30* | (2006.01) |

(52) U.S. Cl.
CPC ........ *A61F 2/4611* (2013.01); *A61B 17/1671* (2013.01); *A61B 17/7077* (2013.01); *A61F 2/4455* (2013.01); *A61B 2090/067* (2016.02); *A61B 2090/3937* (2016.02); *A61F 2002/3013* (2013.01); *A61F 2002/30166* (2013.01); *A61F 2002/30176* (2013.01); *A61F 2002/30179* (2013.01); *A61F 2002/30507* (2013.01); *A61F 2002/30515* (2013.01); *A61F 2002/30538* (2013.01); *A61F 2002/30556* (2013.01)

(58) Field of Classification Search
CPC ........... A61B 2017/0256; A61F 2/4455; A61F 2/4611
See application file for complete search history.

(56) References Cited

U.S. PATENT DOCUMENTS

| | | | |
|---|---|---|---|
| 5,649,926 | A | 7/1997 | Howland |
| 7,655,008 | B2 | 2/2010 | Lenke et al. |
| 7,794,464 | B2 | 9/2010 | Bridwell |
| 8,043,345 | B2 | 10/2011 | Carl et al. |
| 8,221,474 | B2 | 7/2012 | Bridwell et al. |
| 8,277,490 | B2 | 10/2012 | Freeman et al. |
| 2007/0213715 | A1 | 9/2007 | Bridwell et al. |
| 2007/0282443 | A1* | 12/2007 | Globerman ........ A61B 17/1637 623/17.11 |
| 2009/0164018 | A1* | 6/2009 | Sommerich ............... A61F 2/44 623/17.16 |

(Continued)

*Primary Examiner* — Julianna N Harvey

(57) ABSTRACT

A method for treating a spine is provided. The method includes the steps of: disposing an interbody implant adjacent a posterior portion of an intervertebral disc space; connecting a surgical instrument with at least one fixation element fastened with tissue adjacent the posterior portion; and manipulating the surgical instrument such that tissue adjacent the posterior portion engages the interbody implant and one or more vertebra rotate about the interbody implant. Spinal implants, surgical instruments and systems are disclosed.

20 Claims, 18 Drawing Sheets

(56) References Cited

U.S. PATENT DOCUMENTS

| | | | |
|---|---|---|---|
| 2009/0171389 A1* | 7/2009 | Sankaran | A61F 2/4455 606/246 |
| 2011/0082555 A1* | 4/2011 | Martz | A61B 17/1606 623/17.16 |
| 2011/0172714 A1 | 7/2011 | Boachie-Adjei et al. | |
| 2011/0257690 A1 | 10/2011 | Rezach | |
| 2014/0330280 A1* | 11/2014 | Markworth | A61B 17/025 606/90 |

* cited by examiner

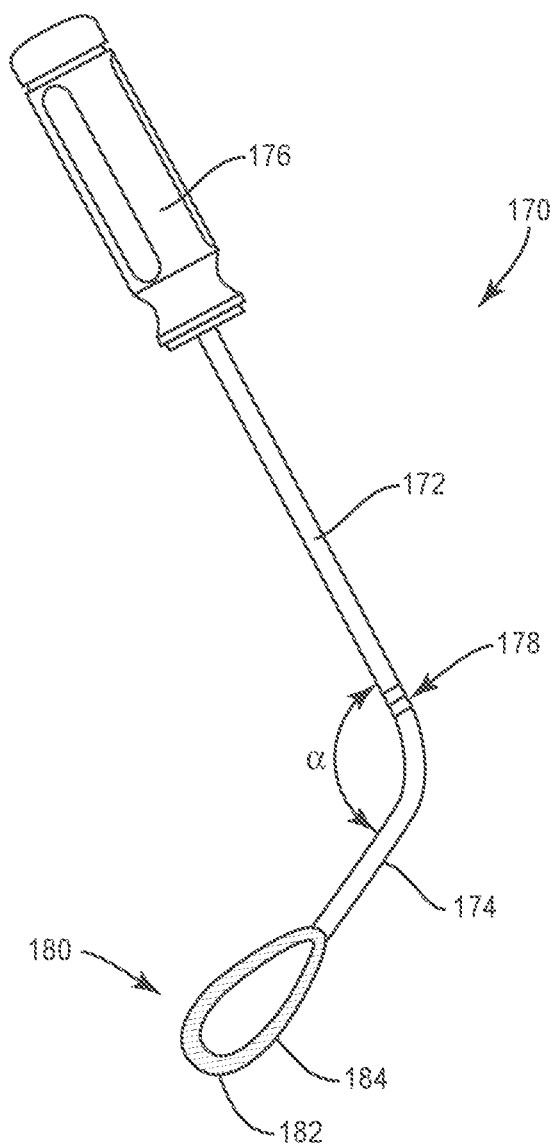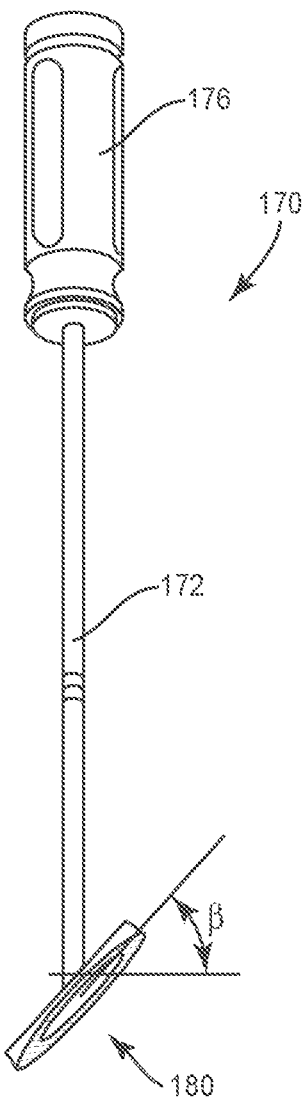
FIG. 18
FIG. 19

SPINAL IMPLANT SYSTEM AND METHOD

CROSS-REFERENCE TO RELATED APPLICATIONS

This application is a divisional of U.S. patent application Ser. No. 14/835,951, filed Aug. 26, 2015, which claims the benefits of U.S. Provisional Patent Application No. 62/105,579 filed Jan. 20, 2015. The contents of these applications are hereby incorporated herein by reference, in their entireties.

TECHNICAL FIELD

The present disclosure generally relates to medical devices for the treatment of musculoskeletal disorders, and more particularly to a surgical system and method for treating a spine.

BACKGROUND

Spinal pathologies and disorders such as degenerative, isthmic and iatrogenic spondylolisthesis, degenerative disc disease, disc herniation, and stenosis may result from disease and degenerative conditions caused by injury, prior surgery and aging. These spinal disorders typically result in symptoms including deformity, pain, nerve damage, and partial or complete loss of mobility. Kyphosis and lysthesis or anterior translation of one vertebra in relation to the next may occur in many of these conditions and pathologies.

Non-surgical treatments, such as medication, rehabilitation and exercise can be effective, however, may fail to relieve the symptoms associated with these disorders. Current evidence based surgical treatment of these spinal disorders includes decompression and restoration of the normal alignment of the spine with concomitant fusion. Techniques used to commonly achieve these goals may include laminectomy, discectomy, internal spinal fixation, correction of the kyphotic deformity and the insertion of implantable interbody prosthetics. As part of these surgical treatments, spinal constructs, such as, for example, bone fasteners, spinal rods and interbody devices can be used to actively correct the pre-existing kyphosis and vertebral translational deformity and to ultimately provide stability to a treated region. For example, during surgical treatment, interbody implants and spinal pedicle screws can be used in concert to correct the abnormal alignment of the spinal vertebrae and provide stability serving to immobilize the spinal motion segment, and with bone graft, will eventually result in a stable fusion. This disclosure describes an improvement in the ability to use interbody and posterior pedicle screw implants to correct spinal kyphotic and translational alignment over prior technologies.

SUMMARY

In one embodiment, a method for treating a spine is provided. The method comprises the steps of: disposing an interbody implant adjacent a posterior portion of an intervertebral disc space; connecting a surgical instrument with at least one fixation element fastened with tissue adjacent the posterior portion; and manipulating the surgical instrument such that tissue adjacent the posterior portion engages the interbody implant and one or more vertebra rotate about the interbody implant. In some embodiments, spinal implants, surgical instruments and systems are provided.

In one embodiment, the method comprises the steps of: disposing an interbody implant in a transverse orientation within the posterior most portion of a surgically evacuated intervertebral disc space; connecting surgical instruments to sagittal angulating pedicle screws fastened to the adjacent vertebrae; and manipulating the surgical instrument such that the posterior portion of the vertebral body endplates engage the interbody implant and one or more vertebra rotate about the interbody implant; thus correcting sagittal misalignment of the vertebrae. In some embodiments, the intervertebral interbody spinal implant is inserted in a transverse orientation within the posterior most portion of the surgically evacuated disc space and it is rotated in the transverse plane so as to reduce a degree of anterior translation of the upper vertebra in relation to the lower.

BRIEF DESCRIPTION OF THE DRAWINGS

The present disclosure will become more readily apparent from the specific description accompanied by the following drawings, in which:

FIG. 18 is a perspective view of components of one embodiment of a system in accordance with the principles of the present disclosure;

FIG. 19 is a side view of the components shown in FIG. 18;

DETAILED DESCRIPTION

Figure 1:
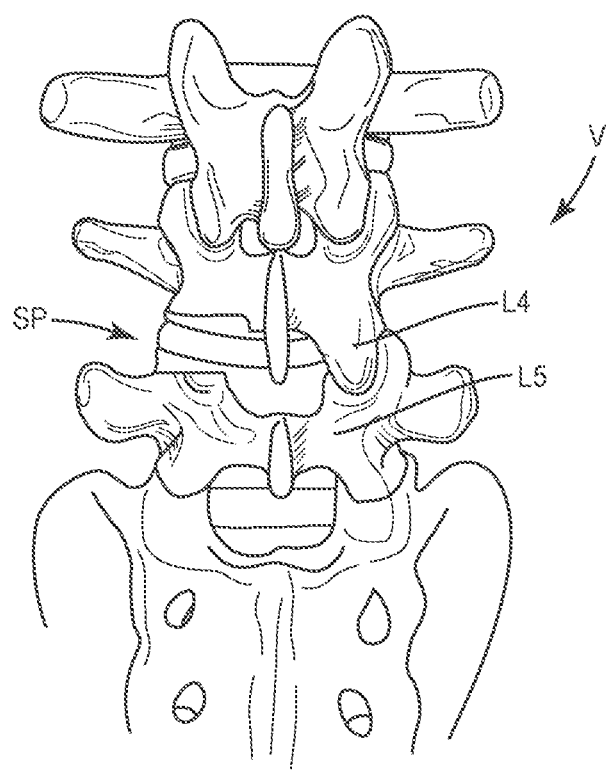
FIG. 1 is a plan view of a spine to be treated with one embodiment of a system in accordance with the principles of the present disclosure.

The exemplary embodiments of the surgical system and related methods of use disclosed are discussed in terms of medical devices for the treatment of musculoskeletal disorders and more particularly, in terms of a surgical system including a spinal implant and a method for treating a spine. In one embodiment, the systems and methods of the present disclosure are employed with a spinal joint fusion, for example, with a cervical, thoracic, lumbar and/or sacral region of a spine. In one embodiment, the spinal implant includes an interbody device, sagittal angulating pedicle screws (SAS), spinal rods and/or bone fasteners.

In some embodiments, the present system is employed with osteotomy techniques and interbody concepts to aid in achieving incremental lumbar lordosis during posterior degenerative fusion procedures. In some embodiments, the present system is employed to optimize segmental lordosis in a trans-foraminal lumbar interbody fusion (TLIF).

In some embodiments, the present system is employed to provide sagittal balance with a resultant improvement in health related quality of life outcomes and the proposed prevention and/or reduction of the incidence of adjacent segment degeneration or proximal junctional kyphosis (PJK). In some embodiments, the present system is employed with a TLIF for treating spondylolithesis and other degenerative conditions. In some embodiments, the present system is employed with a TLIF to achieve consistent, measured lordosis in a spinal segment to be corrected and fused, and/or resist and/or prevent inducement of kyphosis. In some embodiments, the present system is employed to utilize the strength properties of a posterolateral portion of a vertebral endplate adjacent to the pedicles, which resists and/or prevents subsidence of the interbody implant and kyphosis.

In some embodiments, the present system includes a spinal implant comprising an interbody cage that is positioned transversely and rotated in the transverse plane to optimally achieve lordosis, prevent subsidence, and achieve fusion. The location of the implant in a transverse and posterior position in an intervertebral disc space positions the implant on the strong portion of a vertebral endplate while preserving the central and anterior portions of the intervertebral space for bone grafting, biological fusion enhancement, and ultimate fusion. In some embodiments, the present system optimally positions an interbody cage and achieves an optimal measured lordosis of a vertebral segment level with selected interbody cages and surgical instruments that can be employed with open and minimally invasive surgical procedures.

In some embodiments, the present system includes a surgical instrument, such as, for example, a three dimensional interbody cage positioner and rotator. In some embodiments, the present system is employed with a method such that an interbody cage is placed in an intervertebral space from a posterior access and then rotated to a position situated transversely from approximately pedicle to pedicle along a posterior, one-third of a vertebral endplate thus contacting a portion of the endplate that is resistant to subsidence and forming an effective fulcrum for the mechanical creation of lordosis. In some embodiments, the method includes the step of a second rotation such that the cage is rotated in an axial plane, thus the rotation of the cage reduces the degree of the spondylolisthesis as an inferior end plate is pulled back dorsally during the rotation maneuver. In some embodiments, this step indirectly enlarges and decompresses the foramen.

In some embodiments, the present system includes one or more surgical instruments, such as, for example, extenders that effectively extend the length of a beam, such as, for example, a SAS portion of a lever configuration and improve the mechanical advantage of the lever by increasing a distance from a fulcrum, such as, for example, an interbody cage to a pivot point of vertebrae and/or components of the system. In some embodiments, this configuration optimizes lordosis. In some embodiments, a posterior tether connects the extenders and can be slid ventrally towards an interbody cage, thus increasing an angle between the extenders and directly increasing lordosis. In some embodiments, the components of the system are connected to a sliding lordosis gauge. In some embodiments, the lordosis gauge enables an intra-operative direct verification of a degree of lordosis achieved between the pedicle screws and the vertebrae into which they are inserted.

In some embodiments, the present system includes one or more surgical instruments, such as, for example, a cork screw tether, which may be employed with either an open or a minimally invasive approach and that gradually advances a wedge between the extenders in a posterior direction through a cork screw mechanism. As such, an intervertebral disc space is distracted and lordosis is increased at the same time. In some embodiments, the interbody cage is then placed with no instruments obstructing the intervertebral disc space. In some embodiments, the present system includes one or more surgical instruments, such as, for example, a lordosis gauge that can be placed to measure a magnitude of lordosis achieved. In some embodiments, the present system is employed such that its components provide access for bone graft and biologics into an anterior aspect of the intervertebral disc space to facilitate fusion and medical imaging for interpretation of fusion. In some embodiments, the present system includes one or more bone fasteners, such as, for example, a 4.75 or 5.5 millimeters (mm) SAS. In some embodiments, the SAS can be employed for percutaneous applications.

In some embodiments, the present system is employed with a method for treating various indications for arthrodesis in a degenerative lumbar spine, such as, for example, a single level lumbar arthrodesis for degenerative lumbar spondylolisthesis (DLS), isthmic spondylolisthesis (IS) and iatrogenic post-surgical spondylolisthesis, which may include vertebral segments instrumented at any thoracic or lumbar segments but most commonly at the L4-L5 and L5-SI inter-vertebral motion segment. In some embodiments, the present system and method are employed to provide direct neurological element decompression. In some embodiments, the present system and method are employed to provide indirect decompression through restoration of foraminal height, increased disc height and reduction of the degree of lysthesis. In some embodiments, the present system and method are employed to provide solid bony arthrodesis, which may be achieved through interbody anterior load sharing. In some embodiments, the present system and method are employed to provide restoration of segmental lordosis. In some embodiments, the present system and method are employed to provide improvement in lumbar lordosis and/or pelvic incidence ratio, for example, when there is a pre-operative mismatch. In some embodiments, the present system and method are employed to provide a superior endplate of L4 vertebra as an apex of the lumbar lordosis and horizontal on a standing radiographic medical image. In some embodiments, the present system and method are employed to provide lordosis at L4-L5 vertebrae at approximately 20 degrees and at L5-S1 vertebrae at approximately 25 degrees. In some embodiments, the present system and method are employed to provide segmental lordosis at a single level in a range of approximately 20 through 25 degrees.

In some embodiments, the present system is employed with a method for treating L4-L5 vertebrae degenerative, isthmic or iatrogenic spondylolisthesis. In some embodiments, the present system is employed with a method that employs a posterior approach. In some embodiments, the posterior approach may include a posterior midline approach used when a central spinal canal requires decompression or based upon surgeon preference. In some embodiments, the posterior approach may include a posterior bilateral Wiltse muscle splitting approaches. In some embodiments, the posterior approach may include a posterior minimally invasive approach through which superior and inferior facets are accessible or not.

In some embodiments, Wiltse and posterior minimally invasive approaches may be used together; one on one side and one on the other of a spine. In some embodiments, the present system includes posterior pedicle screw instrumentation that is inserted at a single affected motion segment, for example, four screws in two adjacent vertebrae. In some embodiments, the posterior pedicle screw instrumentation may be used at several adjacent or non-contiguous motion segments. In some embodiments, the method includes the step of a postero-lateral disc resection through an interval created by resecting the superior and inferior facets on one or both sides. In some embodiments, a trans-foraminal insertion of an interbody implant with bone with or without biologics such that the interbody implant is inserted in the disc space to obtain an interbody arthrodesis. In some embodiments, the present system and method are employed to provide up to 25 degrees of lordosis at a single vertebral level.

In some embodiments, the present system includes an interbody cage that is positioned transversely and resting on the posterior third of a vertebral endplate, for example, in a region adjacent to the pedicles to resist subsidence. In some embodiments, the present system includes an interbody cage having a clover-leaf design that loads a postero-lateral portion of a vertebral end plate adjacent to the pedicles. In some embodiments, the present system includes bone graft that is placed anteriorly and is easily visualized post-operatively facilitating the assessment of fusion status. In some embodiments, the method includes placing the bone graft anteriorly such that the bone graft is less likely to extrude and displace back into the spinal canal or neural foraminae.

In some embodiments, the present system includes one or more bone fasteners, such as, for example, fixed-angle-screws (FAS), which have a constrained 90 degree angle between the screw shaft and a spinal rod. In some embodiments, the spinal rod is contoured into lordosis such that tightening the FAS orients the screw shaft and the spinal rod to the 90 degree angle to create an anterior column distraction. In some embodiments, the present system and method include selecting an operating room table and positioning of a patient with hips extended to improve lordotic alignment. In some embodiments, the present system and method include placement of the cage transversely in the dorsal one-third of the disc space leaving space within the disc space for bone graft and biologics.

In some embodiments, the present system is employed with a method including the steps of inserting the cage and disc shavers in a first vertical position, for example via straight access, and then rotating the cage 90 degrees to a horizontal or transverse position to minimize root retraction and trauma, for example, of the exiting nerve root. In some embodiments, this configuration is effective at reducing the degree of the spondylolisthesis; restoring disk height; and correcting lateral rotatory lysthesis. In some embodiments, this configuration positions the cage in an optimal area of the vertebral endplate from a strength profile and achieves lordosis. In some embodiments, the present system employs factors, such as, for example, the location of the cage on the endplate, resistance to subsidence and the technique of posterior osteotomy correction to determine sagittal alignment.

In some embodiments, the present system comprise spinal implants including interbody cages that can be modified based on one or more of height, width, length, type and quality of implant bone interface, the position of the cage on the vertebral body endplate, and/or the method of cage insertion.

In some embodiments, the present system comprises an interbody cage including a posteriorly placed transversely oriented dumbbell shaped cage that is placed through a surgical instrument, such as, for example, a three dimensional insertion device. In some embodiments, the cage comprises a dumbbell shape and is inserted from one side in a vertical access direction with a TLIF technique. In some embodiments, once in the disc space, the cage rotates around a horizontal axis into a transverse orientation in the disc space at the back of the vertebral endplate, which may comprise a final resting position.

In some embodiments, the method employed for placement of the cage includes placing the cage in a transverse position so that it is located on the posterior one-third of the vertebral endplate where the bone is most resistant to subsidence. In some embodiments, the cage extends to span from the lateral margin of one pedicle to the lateral margin of the other pedicle. In some embodiments, the final position of the cage is transverse and spans the two strongest portions of the endplate. In some embodiments, the cage is wider than it is high and in some cases from 8-10 mm in height and functions as a fulcrum. In some embodiments, the cage, which is located across the posterior portion of the intervertebral space, is not oversized, and as the cage restores posterior intervertebral height it also by necessity enlarges the intervertebral foraminae. By virtue of the posterior and transverse position of the cage, this foraminal restoration is maintained throughout the processes of compression between the screw heads and lordosis. In some embodiments, the method includes inserting bone graft and biologics anteriorly into the intervertebral space prior to and after the insertion of the cage.

In some embodiments, the present system comprises an interbody cage including a transversely rotating cage placed through a surgical instrument, such as, for example, a three dimensional insertion device. In some embodiments, the method includes the step, after entrance into the disc space posteriorly, as described herein, of rotating the cage, as described herein. In some embodiments, the method includes the step of a second rotation by rotating the cage from a horizontal to a vertical orientation. In some embodiments, the rotation is facilitated by the insertion device, as described herein. In some embodiments, the rotation around a transverse axis achieves an increase in intervertebral height between the two endplates posteriorly, thus creating an effective pivot point which enables the pedicle screws to function as a simple lever arm, and by rotating in the direction opposite to the direction of the antero-listhesis, the degree of the spondylolisthesis is reduced. In some embodiments, the shape of the cage comprises a narrow I-beam that is inserted into an intervertebral disc space in a flat position, thus minimizing the potential interference with the exiting nerve root. In some embodiments, once rotated, the cage is situated transversely across the posterior portion of the endplate, as described herein.

In some embodiments, the present system includes a surgical instrument, such as, for example, a dynamic insertion instrument that enables insertion of the cage into the intervertebral disc in a straight-ahead access. In some embodiments, after insertion, the method includes a first active maneuver that angulates the cage to position it transversely. In some embodiments, the surgical instrument comprises a pivoting control set of levers. In some embodiments, the method includes a second rotation maneuver that enables an increase in the cage height and reduction of the spondylolisthesis. In some embodiments, the insertion instrument rotates the cage with a planetary gear-train, which gives a practitioner a mechanical advantage while allowing the practitioner to perform fine adjustments during the rotation maneuver.

In some embodiments, the present system comprises an interbody cage including a posteriorly expanding cage. In some embodiments, the expanding cage is employed with a method such that the expanding cage is inserted transversely into the intervertebral space, as described herein. In some embodiments, the surgical instrument comprises an inserter having pivoting levers within the inserter handle to enable the cage to be inserted longitudinally and then angled into a transverse position, as described herein. In some embodiments, once the expanding cage is optimally positioned, as described herein, the expanding cage can increase in height through deploying an expanding screw thread. In some embodiments, the expanding cage includes an implant-endplate interface designed to optimize resistance to subsidence. In some embodiments, the expanding cage is positioned with a posterior position of an intervertebral space to allow for access to the intervertebral space to place biologics and bone graft into the desired anterior aspect of the disc space.

In some embodiments, the present system comprises one or more surgical instruments that utilize bone fasteners, such as, for example, a SAS and screw extenders. In some embodiments, multi-axial screws may be employed with the present system.

In some embodiments, the surgical instrument comprises a lever that achieves predictable and measurable lordosis by posterior compression of screw extenders over a posteriorly placed cage acting as a fulcrum. In some embodiments, the lever is used after the cage is placed. In some embodiments, the lever can be used with open or minimally invasive approaches.

In some embodiments, the lever is employed with a method that achieves segmental lordosis through use of a posterior implant and technique that actively controls sagittal alignment. In some embodiments, the lever actively controls the sagittal alignment of the vertebrae while extending the effectiveness of the lever arm and improving the mechanical advantage of a kyphosis correction maneuver. In some embodiments, the lever is employed with a method using a SAS and extenders with a posteriorly placed cage so that cage position is optimized and resistance to subsidence is provided. In some embodiments, this configuration lengthens the lever arm and leaves space for bone graft anterior to the cage. In some embodiments, the lever is connected to a lordosis gauge at an apex of the extenders to accurately measure an intra-operative lordosis achieved. In some embodiments, the apex can be moved closer to the cage by overlapping the extenders and thus shortening the lever arm. In some embodiments, this configuration increases the lordosis achieved and is facilitated by a corkscrew type mechanism that shifts the apex of the extenders ventrally, thus increasing the measureable lordosis angle.

In some embodiments, the extender-lever is attached to a SAS. In some embodiments, the lever is employed with a method using a flat extender with a channel. In some embodiments, the lever is employed with a method that distracts the disc space with a fixture attached to the end of the extenders. In some embodiments, the channel enables tethering with a sliding bolt connector with a goniometer or protractor gauge. In some embodiments, the protractor enables a practitioner to verify the degree of lordosis achieved intra-operatively. In some embodiments, the use of extenders effectively extends the length of the pedicle screw portion of the lever and improves the mechanical advantage of the lever by increasing the distance from the fulcrum (cage) to the pivot point.

In some embodiments, the surgical instrument comprises a cork screw tether, which includes a posterior tethering of extenders to gradually distract an intervertebral disc space in lordotic alignment prior to cage placement using a cork screw controlled wedge held between the screw extenders.

In some embodiments, the cork screw tether is used prior to cage placement. In some embodiments, the cork screw tether can be used with open or minimally invasive approaches.

In some embodiments, the cork screw tether is employed with a method to distract an intervertebral disc space while creating lordosis. In some embodiments, after the screws are placed, a posterior tether is created between the screw extenders, for example, on both sides of vertebrae using four screws and two cork screw tethers. In some embodiments, there is a wedge disposed between the extenders that is actively moved posteriorly in a controlled manner with a cork screw device. In some embodiments, this configuration actively distracts the vertebrae while increasing lordosis. In some embodiments, the method includes facet and disc space releases and spinous process osteotomies to facilitate lordosing distraction. In some embodiments, the cork screw tether includes a goniometer or protractor gauge, as described herein. In some embodiments, combining a bolt-type extender with the threaded tether corkscrew enables the tether to be actively advanced down the channel in the extender, for example, with a cork screw type mechanism, and thus move the tether of the two extenders closer to the fulcrum, for example, an interbody cage and thus increase the lordosis achieved. In some embodiments, the cork screw tether includes a threaded corkscrew handle that can be rotated to incrementally advance the tether down the shaft of the extenders.

In some embodiments, the cork screw tether is employed with a minimally invasive approach and by rotating the cork screw, the tether is advanced ventrally thus increasing the angular kyphosis between the extenders. In some embodiments, the cork screw tether is employed with a minimally invasive approach and the cork screw tether can pull a wedge dorsally between the extenders in a posterior direction while maintaining the posterior tether thus distracting the disc space and increasing lordosis. In some embodiments, a lordosis gage can be placed to measure the magnitude of lordosis achieved.

In some embodiments, the three dimensional cage positioner and rotator is employed with a method such that a cage is placed from a posterior access and then rotated transverse from the pedicles along the posterior one third of the endplate thus contacting the part of the endplate that is most resistant to subsidence and forming an effective fulcrum for the mechanical creation of lordosis. In some embodiments, the method includes the step of a second rotation such that the cage is rotated in an axial plane. As such, the rotation of the cage reduces the degree of the spondylolisthesis as the inferior endplate is pulled back dorsally during the rotation maneuver, which decompresses the foramen.

In some embodiments, the present system and method can be employed through midline exposures, minimally invasive percutaneous and/or lateral Wiltse type incisions, which may include percutaneous systems comprising SAS and extenders. In some embodiments, the present system and method can be employed with a resection of the kissing portion of the posterior spinous processes to facilitate lordosis and enable the sliding of the extender tether ventrally. In some embodiments, the present system and method can be employed with a small midline incision to apply an optoelectronic marker array to the spinous processes for surgical navigation. In some embodiments, through the same incision, the adjacent portions of the spinous processes may be resected to prevent impingement of the spine and inhibition of lordosis.

In some embodiments, the present system includes an interbody cage having a surface, which contacts the vertebral endplate to optimize the bone-implant interface. In some embodiments, the interbody cage surface does not include sharp edges or serrations and may include an interference fit to facilitate porous bony ingrowth. In some embodiments, the method includes disposing bone graft ventral in the anterior and middle third of the intervertebral disc space and thus direct radiographic evidence of fusion as seen on lateral post-operative radiographs.

In some embodiments, the present system includes right-angled down-biting ring and cupped curettes to facilitate safe disc removal transversely across the posterior portion of the intervertebral disc space. In some embodiments, the present system includes markers on the surgical instruments to resist and/or prevent placement into the spinal canal and/or outside the protective annulus of the intervertebral disc.

In some embodiments, the present system includes angled ronguers for removal of intervertebral disc tissue. In some embodiments, the present system includes ring and cupped curettes for anterior disc tissue removal and separate angled instruments for posterior disc tissue removal. In some embodiments, the present system includes a distractor to facilitate anterior release of the intervertebral disc space, for example, for deformity correction. In some embodiments, the present system includes rod benders and pre-contoured rods with increased diameter bends to facilitate lordosis. In some embodiments, the present system is employed with a method to treat single level degenerative applications and utilize 4.75 and 5.5 mm bone fasteners. In some embodiments, the present system is employed with a method employing a SAS for percutaneous applications. In some embodiments, the present system is employed with a method employing lever extenders, corkscrew extenders and gauges that can be used with 4.75 mm and 5.5 mm bone fasteners.

In some embodiments, the present system is employed with a method employing transversely placed posterior endplate cages. In some embodiments, the cages can include expanding cages, insert-angulate-and-rotate cages, and/or cages connected with an angled inserter.

In some embodiments, the present system and method are employed for optimizing segmental lordosis in TLIF procedures. In some embodiments, the present system is employed with a method comprising the steps of: placing an interbody fusion implant laterally in the posterior one-third of an intervertebral disc space via a unilateral TLIF approach; using a surgical instrument attached to posterior fixation elements, such as, for example, pedicle screws and/or screw extenders, to exert a compressive force on the interbody fusion implant; and using the interbody fusion implant as a posterior fulcrum to achieve segmental lordosis at the fusion level.

In some embodiments, the present system may include allograft and/or other bone growth promoting material. In some embodiments, the present system may include allograft and/or other bone growth promoting material, which may be added via a TLIF approach and packed into an intervertebral disc space anterior to an interbody fusion implant. In some embodiments, the present system may include an interbody fusion implant that comprises a cylindrical barbell shape. In some embodiments, the present system may include an interbody fusion implant that comprises a taller than wide rectangular box or I-beam shape. In some embodiments, the present system may include an interbody fusion implant that comprises an expandable height implant.

In some embodiments, the present system is employed with a method comprising the steps of: inserting one or more interbody fusion implants, rotating the implants; and exerting a compressive lordosing force on posterior screws. In some embodiments, the present system is employed with a method comprising the steps of: placing a laterally-oriented TLIF implant, such as, for example, a banana-shaped cage, on the posterior one-third of the vertebral endplate to introduce lordosis at any one spinal segment. In some embodiments, the present system includes specialized surgical instruments for inserting the implants, rotating the implants and exerting a compressive lordosing force on posterior screws.

The present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. Also, in some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

As used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, micro discectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, muscle, ligaments, tendons, cartilage and/or bone unless specifically referred to otherwise.

The following discussion includes a description of a surgical system and related methods of employing the surgical system in accordance with the principles of the present disclosure. Alternate embodiments are also disclosed. Reference is made in detail to the exemplary embodiments of the present disclosure, which are illustrated in the accompanying figures. Turning to FIGS. 1-11, there are illustrated components of a surgical system, such as, for example, a spinal implant system 10.

The components of spinal implant system 10 can be fabricated from biologically acceptable materials suitable for medical applications, including metals, synthetic polymers, ceramics and bone material and/or their composites. For example, the components of spinal implant system 10, individually or collectively, can be fabricated from materials such as stainless steel alloys, commercially pure titanium, titanium alloys, Grade 5 titanium, superelastic titanium alloys, cobalt-chrome alloys, stainless steel alloys, superelastic metallic alloys (e.g., Nitinol, super elasto-plastic metals, such as GUM METAL®), ceramics and composites thereof such as calcium phosphate (e.g., SKELITE™), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate such as hydroxyapatite (HA), corraline HA, biphasic calcium phosphate, tricalcium phosphate, or fluorapatite, tri-calcium phosphate (TCP), HA-TCP, calcium sulfate, or other resorbable polymers such as polyaetide, polyglycolide, polytyrosine carbonate, polycaroplaetohe and their combinations, biocompatible ceramics, mineralized collagen, bioactive glasses, porous metals, bone particles, bone fibers, morselized bone chips, bone morphogenetic proteins (BMP), such as BMP-2, BMP-4, BMP-7, rhBMP-2, or rhBMP-7, demineralized bone matrix (DBM), transforming growth factors (TGF, e.g., TGF-3), osteoblast cells, growth and differentiation factor (GDF), insulin-like growth factor 1, platelet-derived growth factor, fibroblast growth factor, or any combination thereof.

Various components of spinal implant system 10 may have material composites, including the above materials, to achieve various desired characteristics such as strength, rigidity, elasticity, compliance, biomechanical performance, durability and radiolucency or imaging preference. The components of spinal implant system 10, individually or collectively, may also be fabricated from a heterogeneous material such as a combination of two or more of the above-described materials. The components of spinal implant system 10 may be monolithically formed, integrally connected or include fastening elements and/or instruments, as described herein. In one embodiment, a spinal implant, as described herein, may be formed substantially of a biocompatible metal, such as titanium and selectively coated with a bone-growth promoting material, such as HA. In one embodiment, a spinal implant, as described herein, may be formed substantially of a biocompatible polymer, such as PEEK, and selectively coated with a biocompatible metal, such as titanium, or a bone-growth promoting material, such as HA. In some embodiments, titanium may be plasma sprayed onto surfaces of the spinal implant to modify a radiographic signature of the spinal implant and/or improve bony ongrowth to the spinal implant by application of a porous or semi-porous coating of titanium.

Figure 7:
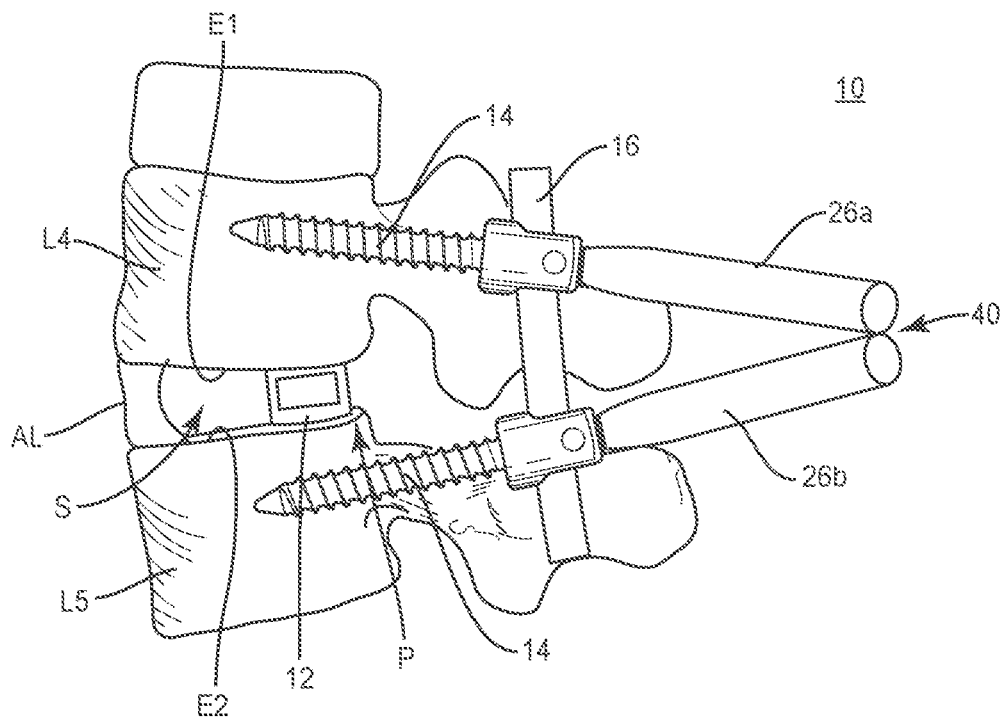
FIG. 7 is a break away side view of components of one embodiment of a system in accordance with the principles of the present disclosure disposed with vertebrae.

Spinal implant system 10 may be employed, for example, with minimally invasive procedures, including percutaneous techniques, mini-open surgical techniques and/or open surgical techniques to deliver and introduce instrumentation and/or spinal implants, such as, for example, an interbody implant, such as, for example, a cage 12, as shown in FIG. 7, at a surgical site within a body of a patient, which includes, for example, vertebrae V. In some embodiments, spinal implant system 10 can include spinal constructs including one or more bone fasteners, such as, for example, SAS 14, spinal rods 16, tethers, connectors, plates and/or instruments, as described herein. In some embodiments, various components of spinal implant system 10 may be utilized in open or traditional spinal surgical techniques. In some embodiments, spinal implant system 10 is employed to achieve consistent, measured lordosis in a spinal segment of vertebrae V to be corrected and fused, and/or resist and/or prevent inducement of kyphosis. In some embodiments, spinal implant system 10 is employed to utilize the strength properties of a posterior and/or postero-lateral portion of a vertebral endplate of vertebrae V adjacent to the pedicles, which resists and/or prevents subsidence and kyphosis.

Figure 2:
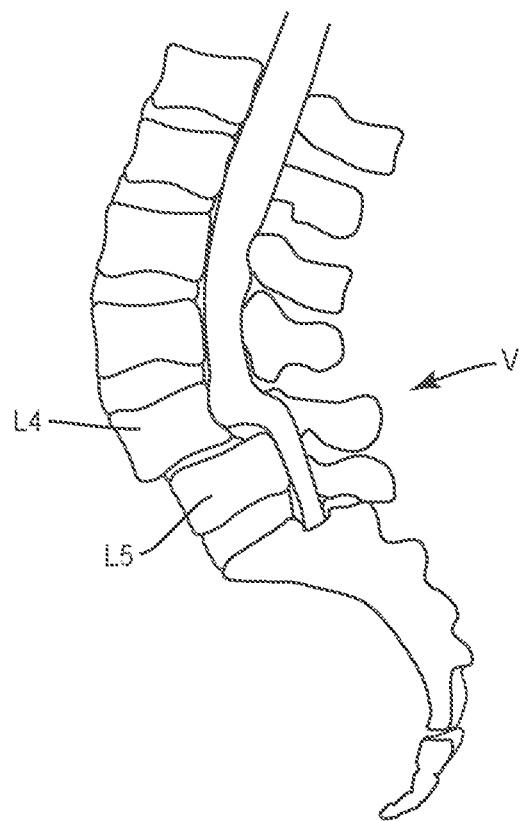
FIG. 2 is a lateral view of the spine shown in FIG. 1.

In some embodiments, spinal implant system 10 is employed with a TLIF surgical approach, technique or procedure, which utilizes an opening in bone, such as, for example, foramina between a vertebral body, such as, for example, vertebra L4 and a vertebral body, such as, for example, vertebra L5, as shown in FIGS. 1 and 2. While some examples shown herein depict L4 and L5, it should be understood that the various embodiments could be used in procedures for the treatment of any selected levels of the human spine, including the cervical spine, thoracic spine and/or lumbar spine (including but not limited to the L5-S1 (lumbosacral) disc space. In some embodiments, a patient is positioned in a prone position. In some embodiments, the TLIF procedure includes an inter-muscular/Wiltse approach such that adjacent muscle is dissected. In this approach, a para-spinal incision is made to provide exposure to the surgical site, such as, for example, a lumbo-sacral junction. In some embodiments, spinal implant system 10 is employed with a patient in a prone position, and/or employed with various additional surgical approaches to the spine, including anterior, posterior, posterior mid-line, direct lateral, postero-lateral, and/or antero lateral approaches.

Figure 3:
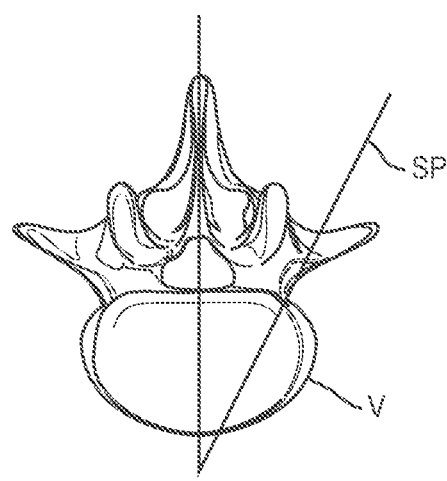
FIG. 3 is an axial view of the spine shown in FIG. 1.
Figure 4:
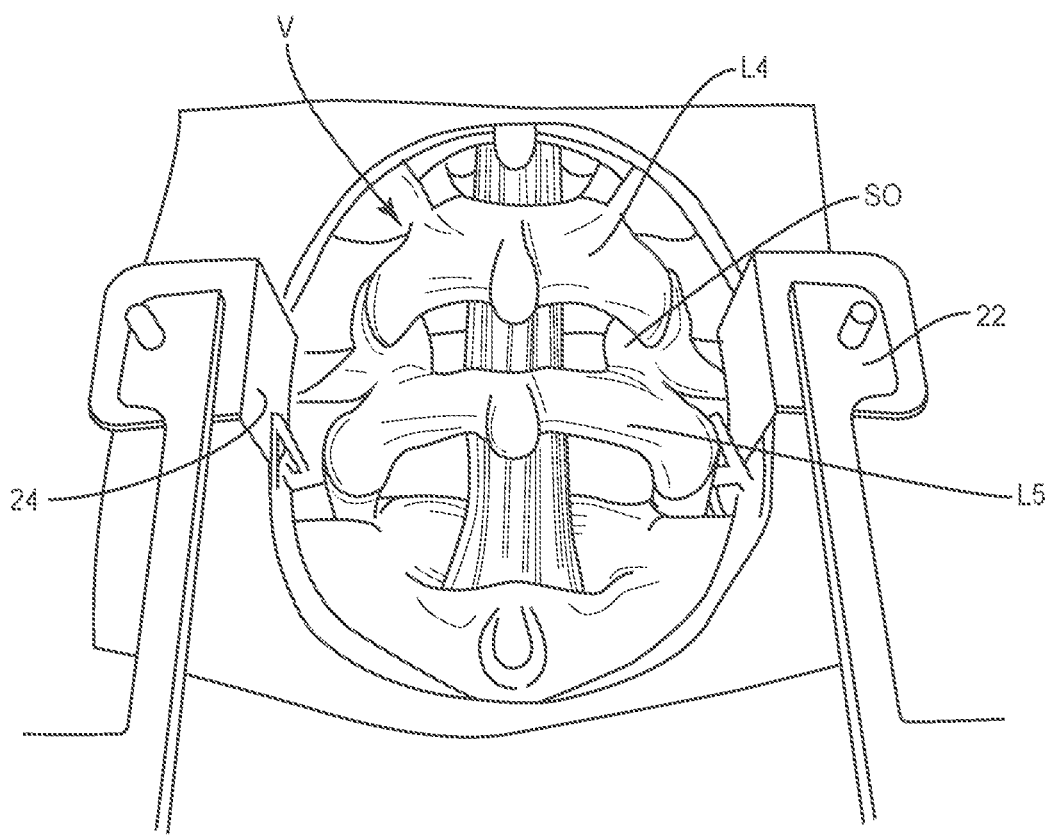
FIG. 4 is a plan view of components of one embodiment of a system in accordance with the principles of the present disclosure disposed with vertebrae.

In some embodiments, in connection with the TLIF procedure, a medical practitioner makes and/or creates an incision in tissue, which includes soft tissue and/or muscle, to obtain access to a surgical site including vertebral levels L4, L5. Retractor 22, as shown in FIG. 4, is inserted through the incision and disposed with the tissue. Blades 24 of retractor 22 engage and space the tissue to create a surgical pathway and/or opening SO to the surgical site, which includes a surgical pathway SP, as shown in FIG. 3, employed with the TLIF surgical approach.

Once access to the surgical site is obtained, a surgical procedure, as described herein, is performed for treating the spine disorder. The diseased and/or damaged portion of vertebrae V, which may include diseased and/or damaged intervertebral disc tissue, are removed to create a vertebral space between vertebrae L4, L5.

In some embodiments, pilot holes are made in selected vertebra of vertebrae V for receiving fixation elements, such as, for example, bone fasteners. For example, each of SAS 14 is inserted or otherwise engaged with each of vertebrae L4, L5. In some embodiments, spinal constructs including rods 16 are employed as provisional and/or working rods to support vertebrae V during a surgical procedure. One or more rods 16 are connected and reduced with receivers of SAS 14 to provide support and stabilization of vertebrae L4, L5. In some embodiments, spinal implant system 10 may include one or a plurality of the spinal constructs. In some embodiments, the plurality of spinal constructs may be disposed in various alternate orientations, such as, for example, side by side, parallel, transverse and/or other angular orientations such as acute or obtuse, co-axial and/or may be offset or staggered. In some embodiments, the plurality of spinal constructs including rods 16 may provide a template configuration for permanently implantable spinal rods, such as, implantable, final, permanent, removable, non-removable, bio-absorbable, resorbable and/or bio-degradable, and/or comprise permanently implantable spinal rods.

Figure 5:
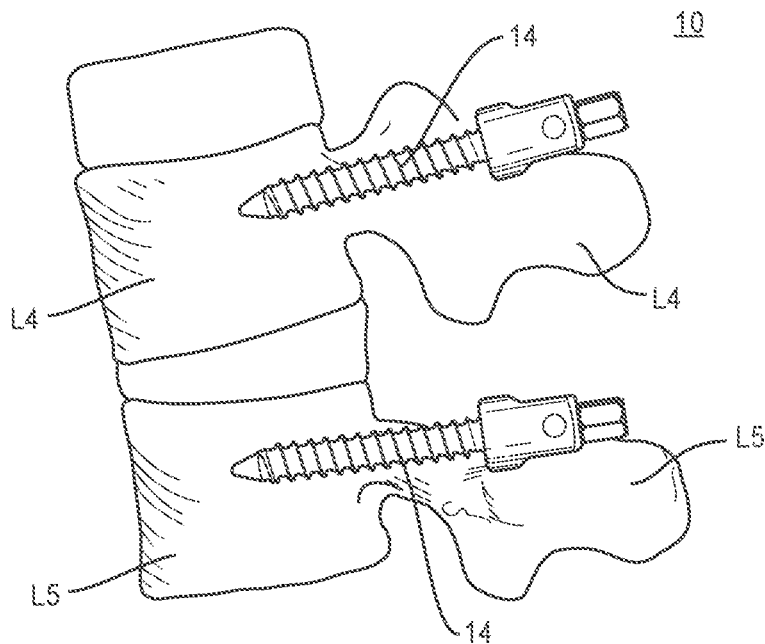
FIG. 5 is a break away side view of components of one embodiment of a system in accordance with the principles of the present disclosure disposed with vertebrae.
Figure 6:
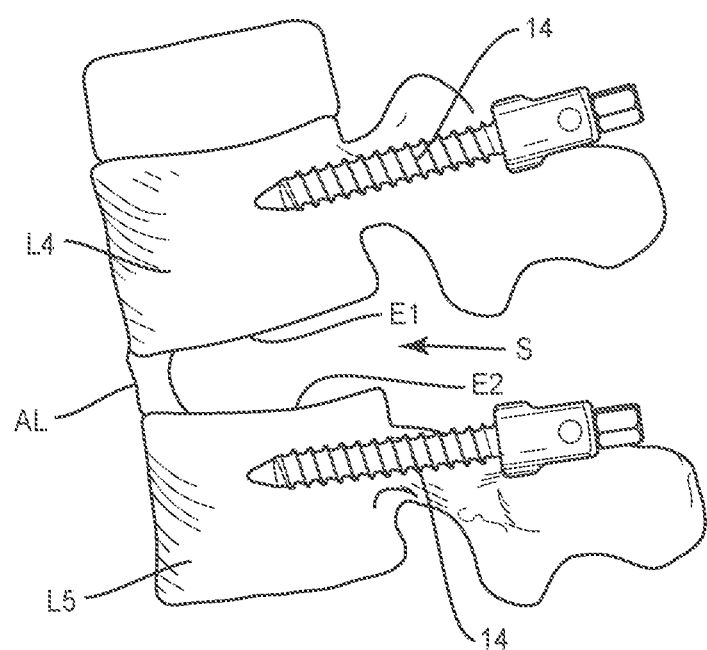
FIG. 6 is a side view of the components and vertebrae shown in FIG. 5.
Figure 20:
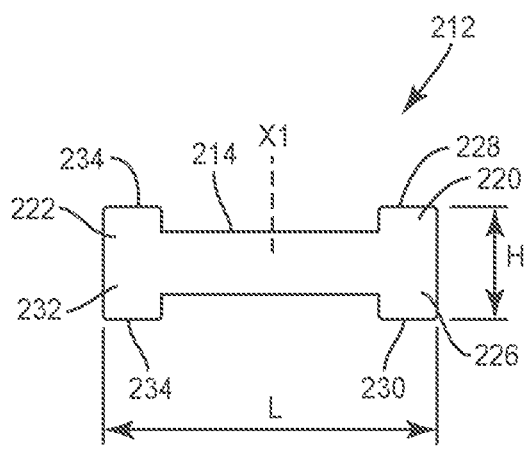
FIG. 20 is a side view of components of one embodiment of a system in accordance with the principles of the present disclosure.
Figure 21:
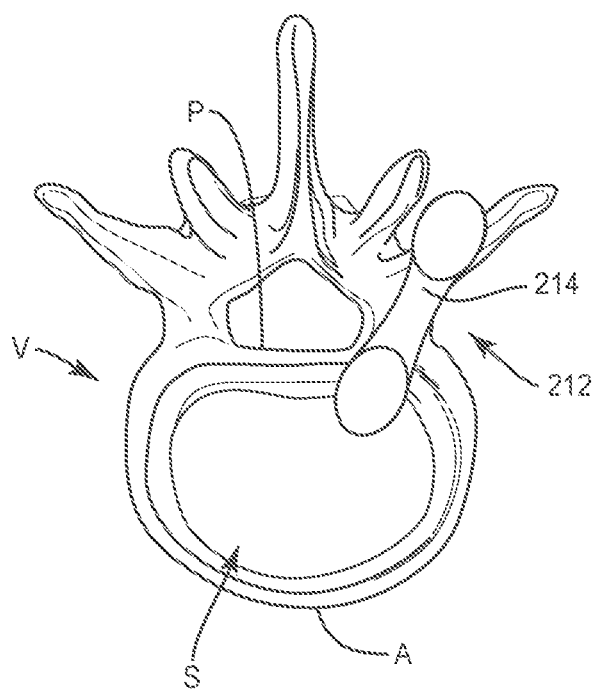
FIG. 21 is a plan view of components of one embodiment of a system in accordance with the principles of the present disclosure disposed with vertebrae.

A preparation instrument (for example, as shown in FIGS. 20 and 21) is employed to remove disc tissue, fluids, adjacent tissues and/or bone, and scrape and/or remove tissue from endplate surfaces E1 of vertebra L4 and/or endplate surface E2 of vertebra L5. Vertebral facets, such as, for example, an L4 inferior facet and an L5 superior facet are resected, as shown in FIG. 5. A trans-foraminal discectomy is performed to create vertebral space S between vertebral bodies L4, L5 leaving a portion of an anterior ligament AL, as shown in FIG. 6.

In some embodiments, the size of cage 12 is selected after trialing. In some embodiments, cage 12 is visualized by fluoroscopy and oriented before introduction into vertebral space S. A surgical instrument, such as, for example, an inserter (not shown) is connected with cage 12 for disposal in an introduction or delivery orientation for alignment of cage 12 with the surgical pathway SP such that cage 12 is steerable to vertebral space S between vertebrae L4, L5. In some embodiments, manipulation of the inserter rotates and/or steers cage 12. Cage 12 is selectively positioned to an implantable orientation adjacent a posterior portion P of vertebral space S between vertebrae L4, L5, as shown in FIG. 7.

Cage 12 is inserted into vertebral space S between vertebrae L4, L5 to re-establish and maintain disc height. Cage 12 is disposed posteriorly within vertebral space S adjacent posterior portion P and the pedicles of vertebrae L4, L5. In some embodiments, this configuration of cage 12 and selective orientation of cage 12 with vertebrae L4, L5 aligns cage 12 with the portion of a vertebral endplate having a higher strength and resistance to subsidence. In some embodiments, posterior placement of cage 12 provides space within vertebral space S for disposal of bone graft and/or other agents, as described herein. Posterior placement of cage 12 improves stability and decreases the risk of subsidence into tissue, as described herein. In some embodiments, cage 12 provides height restoration between vertebral bodies, decompression, and restoration of sagittal and/or coronal balance. In some embodiments, an inserter (not shown) is connected with cage 12 to rotate cage 12, in the direction shown by arrow R (and/or in an opposite direction) in FIG. 9. The height of cage 12 is increased and the end surfaces of cage 12 rotate into engagement with endplate surface E1 of vertebra L4 and endplate surface E2 of vertebra L5, such that surfaces E1, E2 exert a compressive force on cage 12.

In some embodiments, alignment and disposal of cage 12 with posterior portion P orients cage 12 such that it comprises a fulcrum. The fulcrum configuration of cage 12 is disposed between and engages endplate surfaces E1, E2. A surgical instrument, as described herein, is connected with vertebrae L4, L5 to manipulate vertebrae L4, L5 such that endplate surfaces E1, E2 adjacent posterior portion P engage cage 12, disposed in a fulcrum configuration. For example, manipulating the surgical instrument causes endplate surfaces E1, E2 adjacent posterior portion P to exert a compressive force on cage 12 such that cage 12 comprises a posterior fulcrum during posterior compression and vertebrae L4, L5 are selectively rotated about cage 12 to achieve a measured lordosis in the L4, L5 spinal segment.

Figure 8:
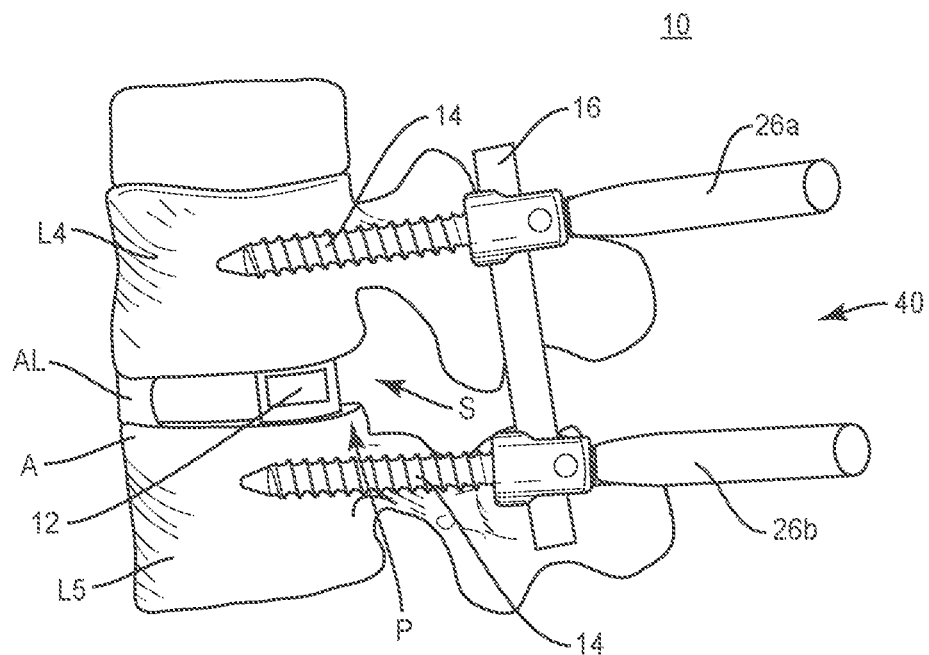
FIG. 8 is a side view of the components and vertebrae shown in FIG. 7.
Figure 9:
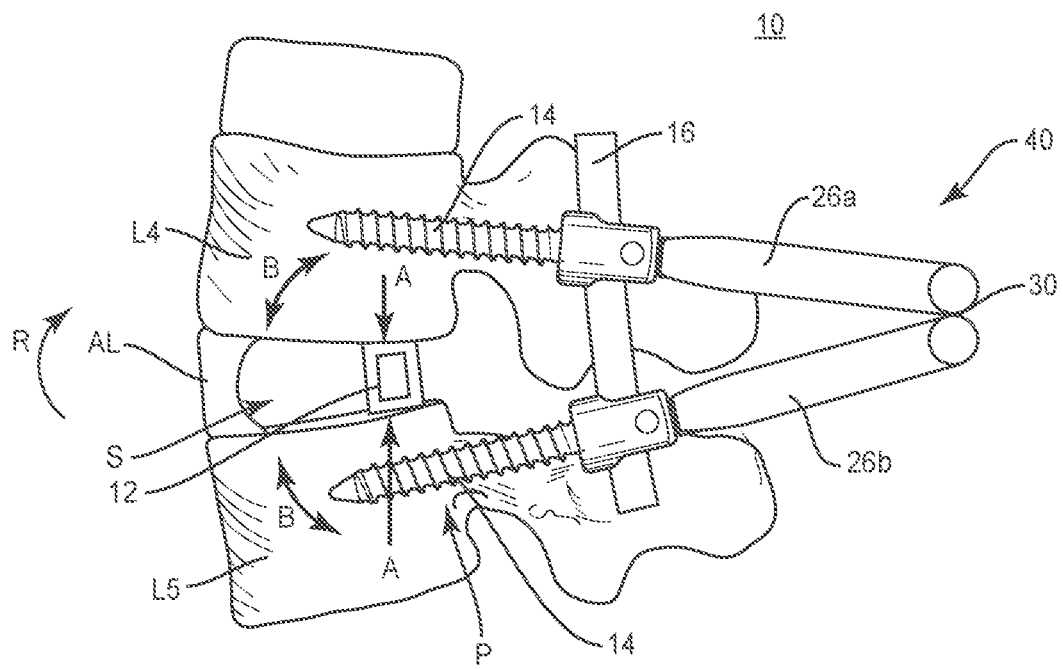
FIG. 9 is a side view of the components and vertebrae shown in FIG. 7.
Figure 10:
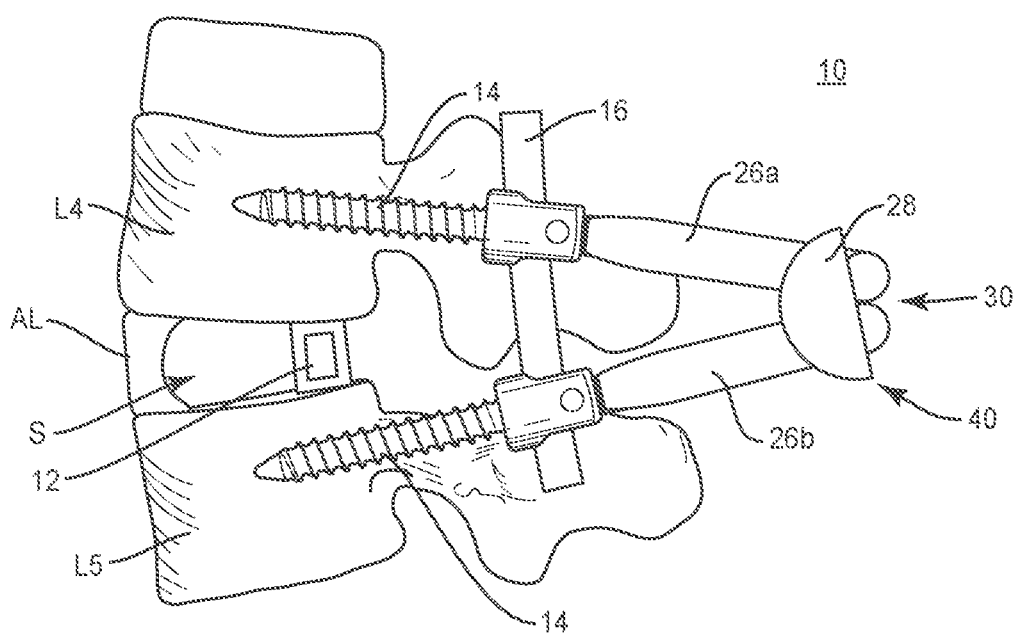
FIG. 10 is a break away side view of components of one embodiment of a system in accordance with the principles of the present disclosure disposed with vertebrae.
Figure 11:
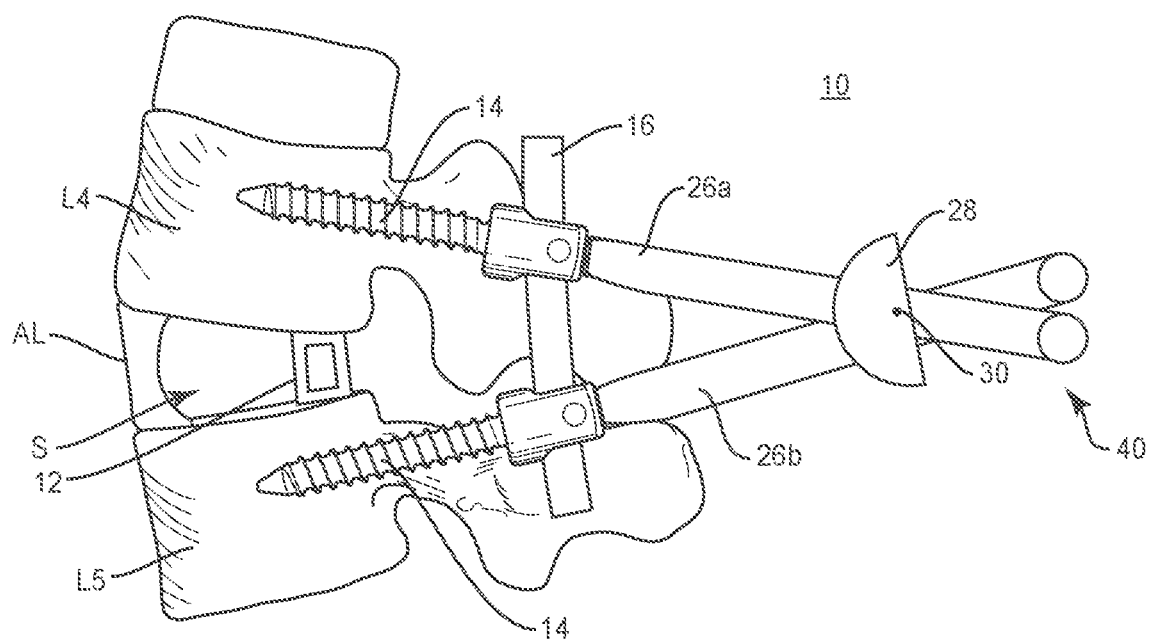
FIG. 11 is a side view of the components and vertebrae shown in FIG. 10.

In some embodiments, a surgical instrument 40, as shown in FIGS. 7-9, is employed to manipulate vertebrae L4, L5. Surgical instrument 40 includes lever arms, such as, for example, extenders 26*a*, 26*b*. Extenders 26*a*, 26*b* are attached with SAS 14 to manipulate vertebrae L4, L5. Surgical instrument 40 manipulates vertebrae L4, L5 such that endplate surfaces E1, E2 adjacent posterior portion P exert a compressive force, in the direction shown by arrows A in FIG. 9, on cage 12 such that cage 12 comprises a posterior fulcrum during posterior compression. As such, surgical instrument 40 manipulates vertebrae L4, L5 to selectively rotate vertebrae L4, L5, in the direction shown by arrows B in FIG. 9, about cage 12 to achieve segmental lordosis of vertebrae L4, L5. In some embodiments, surgical instrument 40 includes a lordosis gauge 28, as shown in FIG. 10, attached to extenders 26 at an apex 30 of extenders 26 to measure lordosis, for example in an angular representation of degrees, as provided by the components of spinal implant system 10 and described herein. In one embodiment, apex 30 can be adjusted by overlapping extenders 26 to shorten/lengthen lever arms 26*a*, 26*b* and the distance from vertebrae L4, L5 to increase/decrease lordosis, as shown in FIG. 11. Extenders 26*a*, 26*b*, as shown in FIG. 11, are shown in simple schematic form but may take the form of one or more slotted extenders that may be removably and/or selectively attached to a receiver head on SAS 14 or any other bone and/or pedicle screw.

Upon completion of a procedure, as described herein, the surgical instruments, assemblies and non-implanted components of spinal implant system 10 are removed and the incision(s) are closed. One or more of the components of spinal implant system 10 can be made of radiolucent materials such as polymers. Radiopaque markers may be included for identification under x-ray, fluoroscopy, CT or other imaging techniques. In some embodiments, the use of surgical navigation, microsurgical and image guided technologies may be employed to access, view and repair spinal deterioration or damage, with the aid of spinal implant system 10. In some embodiments, spinal implant system 10 may include one or a plurality of interbody implants, rods, tethers, plates, connectors and/or bone fasteners for use with a single vertebral level or a plurality of vertebral levels. In some embodiments, spinal implant system 10 may include one or a plurality of bone fasteners that may comprise multi-axial screws, sagittal angulation screws, pedicle screws, mono-axial screws, uni-planar screws, facet screws, fixed screws, tissue penetrating screws, conventional screws, expanding screws, wedges, anchors, buttons, dips, snaps, friction fittings, compressive fittings, expanding rivets, staples, nails, adhesives, posts, fixation plates and/or posts.

In one embodiment, spinal implant system 10 includes an agent, which may be disposed, packed, coated or layered within, on, adjacent or about the components and/or surfaces of spinal implant system 10, and/or disposed with tissue. In some embodiments, the agent may include bone growth promoting material, such as, for example, bone graft to enhance fixation of the components and/or surfaces of spinal implant system 10 with vertebrae. In some embodiments, the agent may include one or a plurality of therapeutic agents and/or pharmacological agents for release, including sustained release, to treat, for example, pain, inflammation and degeneration.

Figure 12:
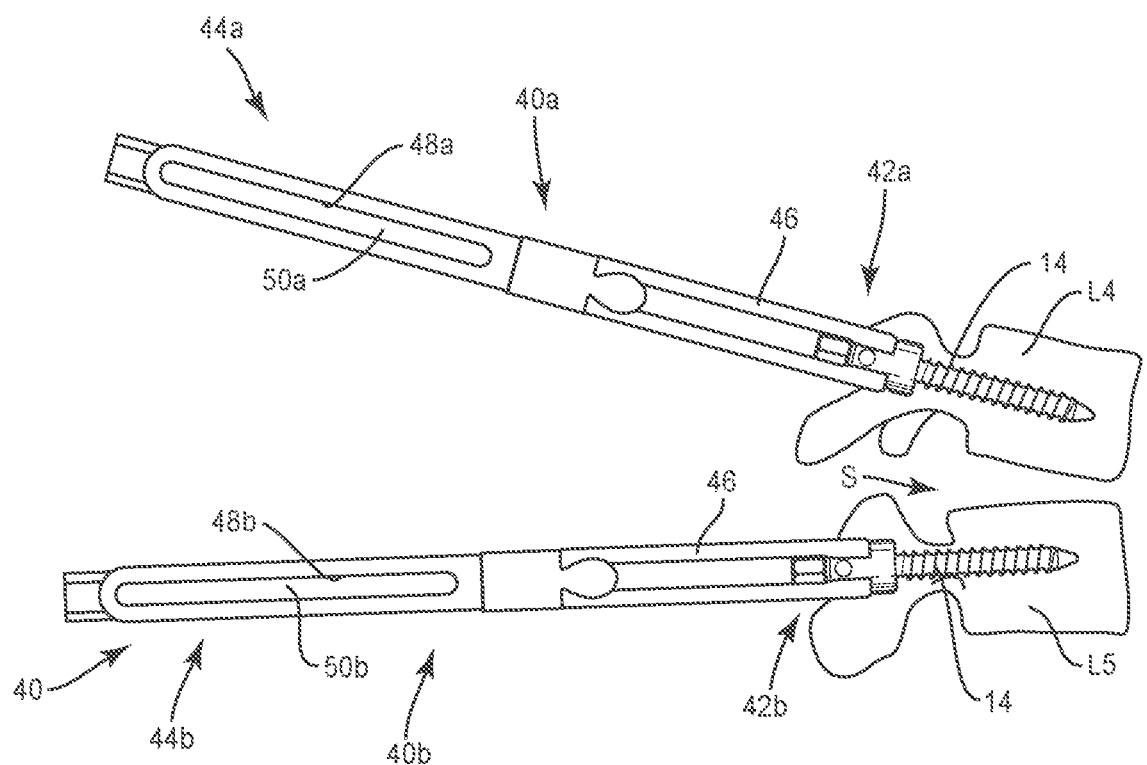
FIG. 12 is a break away side view of components of one embodiment of a system in accordance with the principles of the present disclosure disposed with vertebrae.
Figure 13:
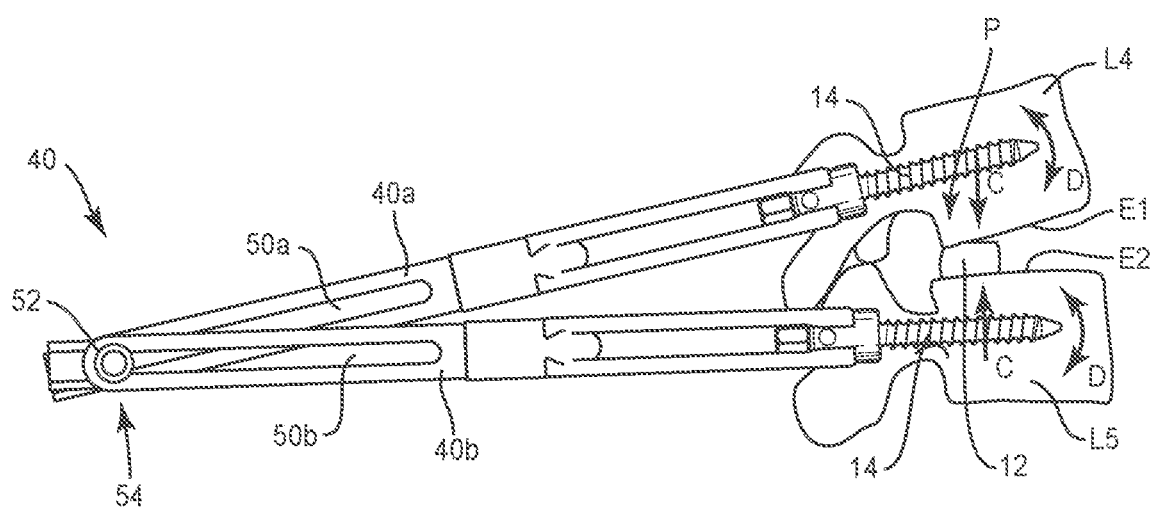
FIG. 13 is a break away side view of components of one embodiment of a system in accordance with the principles of the present disclosure disposed with vertebrae.
Figure 14:
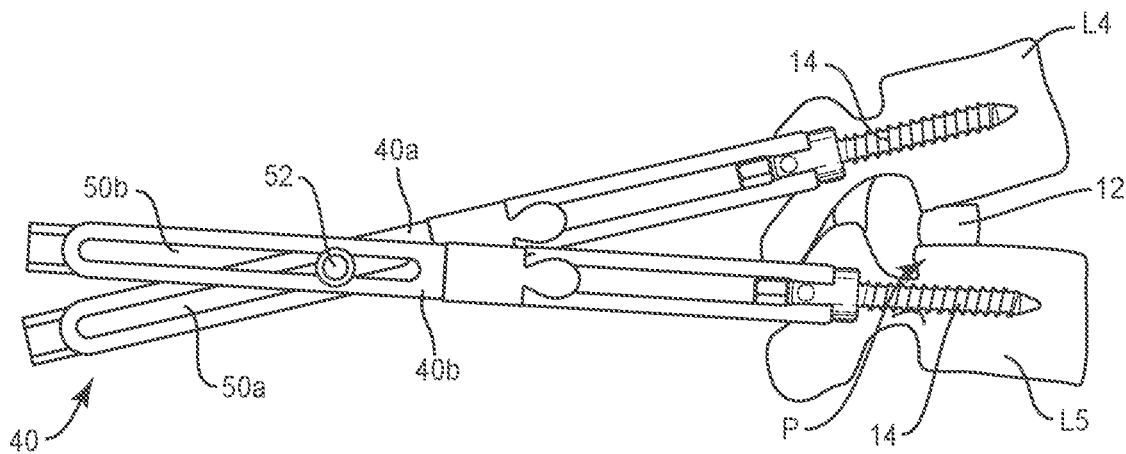
FIG. 14 is a side view of the components and vertebrae shown in FIG. 13.

In one embodiment, as shown in FIGS. 12-14, surgical instrument 40, similar to that described above, includes arms 40*a*, 40*b*. Arm 40*a* extends between an end 42*a* and an end 44*a*. End 42*a* includes an extender 46 configured for engagement with SAS 14 at vertebra L4, similar to that described herein. End 44*a* includes a flat configuration having a surface 48*a* that defines a channel 50*a*. Arm 40*b* extends between an end 42*b* and an end 44*b*. End 42*a* includes an extender 46 configured for engagement with SAS 14 at vertebra L5, similar to that described herein. End 44*b* includes a flat configuration having a surface 48*b* that defines a channel 50*b*. In some embodiments, extender 46 may be connected, attached or monolithically formed with arm 40*a* and/or arm 40*b*. In some embodiments, channel 50*a* and/or channel 50*b* may have various configurations, such as, for example, oval, oblong, rectangular, polygonal, irregular, uniform, non-uniform, variable and/or tapered. Channels 50*a*, 50*b* are configured for movable disposal of a connector, such as, for example, a bolt 52. Bolt 52 is translatable along channels 50*a*, 50*b*, and configured to facilitate relative translation and/or rotation of arms 40*a*, 40*b*. In some embodiments, bolt 52 includes a lock for fixing relative position of arms 40*a*, 40*b*.

Surgical instrument 40, as shown in FIGS. 12-14, is employed to manipulate vertebrae L4, L5. Arms 40*a*, 40*b* are attached with SAS 14, via extenders 46, to manipulate vertebrae L4, L5 such that endplate surfaces E1, E2 adjacent posterior portion P exert a compressive force, in the direction shown by arrows C in FIG. 13, on cage 12 such that cage 12 comprises a posterior fulcrum during posterior compression. As such, arms 40*a*, 40*b* manipulate vertebrae L4, L5 to selectively rotate vertebrae L4, L5, in the direction shown by arrows D in FIG. 13, about cage 12 to achieve segmental lordosis of vertebrae L4, L5. In some embodiments, as shown in FIG. 14, bolt 52 is configured to translate along channels 50*a*, 50*b* to adjust and overlap extenders 46 to shorten/lengthen arms 40*a*, 40*b* and the distance from vertebrae L4, L5 to increase and/or decrease an apex 54 of arms 40*a*, 40*b* to increase/decrease lordosis.

Figure 15:
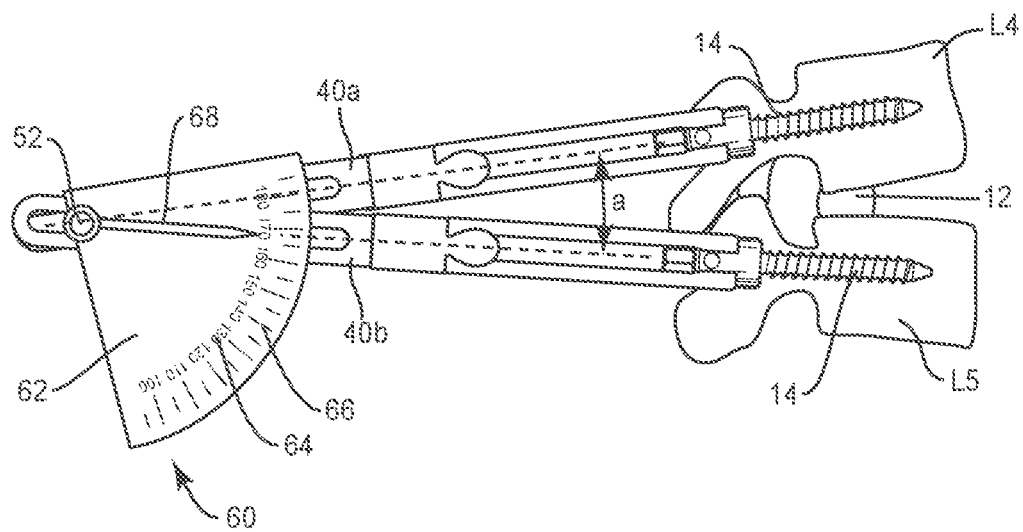
FIG. 15 is a break away side view of components of one embodiment of a system in accordance with the principles of the present disclosure disposed with vertebrae.

In one embodiment, as shown in FIG. 15, instrument 40 includes a lordosis gauge, such as, for example, a protractor 60, Protractor 60 is configured to facilitate determination of the degree of lordosis achieved intra-operatively. In one embodiment, protractor 60 is configured for attachment to bolt 52, described herein. In some embodiments, protractor 60 can be connected, attached or monolithically formed with arms 40*a*, 40*b*, described herein. Protractor 60 includes an outer surface 62 that includes indicia 64 that represents and/or provides information relating to the segmental lordosis of vertebrae L4, L5. In some embodiments, indicia 64 include markings 66 that comprise a plurality of spaced apart graduations.

Markings 66 represent and/or provide information relating to an angular range for measuring, selecting, adjusting and/or displaying an angle a between arms 40a, 40b connected with vertebrae L4, L5 connected thereto. In some embodiments, angle a is measured in a range of 0 through 40 degrees. An indicator, such as, for example, a pointer 68 identifies a measured, selected, adjusted and/or displayed angle from surface 62. Markings 66 include bi-laterally disposed grooves equidistantly spaced apart and corresponding to measured angular increments of indicia 64. Pointer 68 is movable relative to surface 62 and markings 66 to identify a measured, selected, adjusted and/or displayed angle from surface 62 between vertebrae L4, L5 connected thereto.

In some embodiments, markings 66 are disposed in increments of 10 angular degrees. In some embodiments, indicia 64 may include an analog, such as, for example, a dial with a numerical indicator of angle and/or digital display, such as, for example, LED and/or LCD. In some embodiments, indicia 64 include human readable visual indicia, such as, for example, a label, color coding, alphanumeric characters or an icon. In some embodiments, indicia 64 include human readable tactile indicia, such as, for example, raised portions, lowered portions or Braille. In some embodiments, indicia 64 is a printed or written item in combination with a slot or groove, whereby the printed or written item is placed in the slot or groove to display information. In some embodiments, indicia 64 may be applied as an adhesive. In some embodiments, surface 62 is disposed at an angular orientation, for example 90 degrees, relative to a longitudinal axis of extenders 46, such that indicia 64 is disposed at an angular orientation, for example 90 degrees, relative to the longitudinal axis to display information to a medical practitioner. In some embodiments, this configuration enables a surgeon with a dorsal line of sight, for example from above indicia 64, to read the displayed information of indicia 64.

Figure 16:
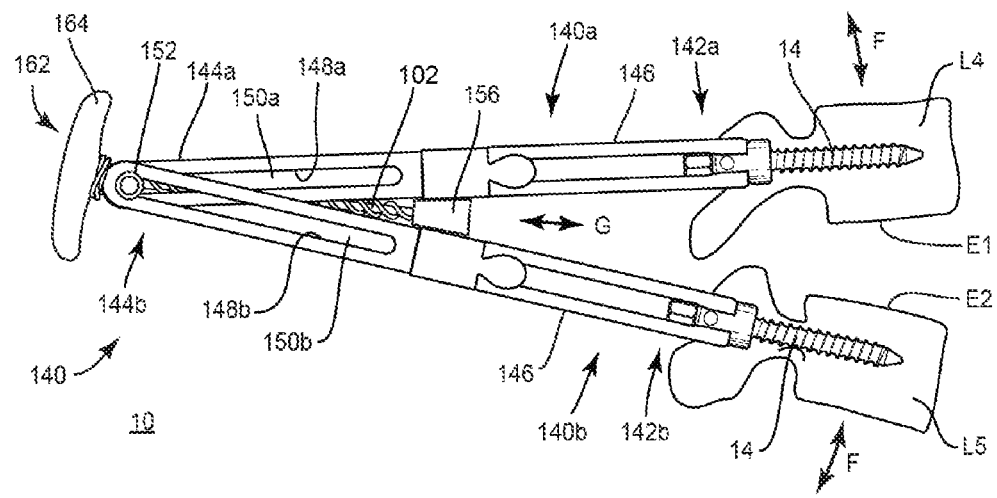
FIG. 16 is a break away side view of components of one embodiment of a system in accordance with the principles of the present disclosure disposed with vertebrae.
Figure 17:
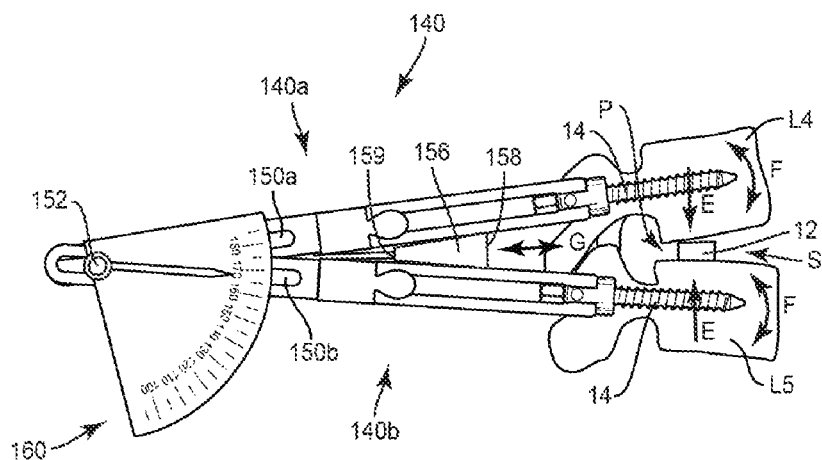
FIG. 17 is a break away side view of components of one embodiment of a system in accordance with the principles of the present disclosure disposed with vertebrae.

In one embodiment, as shown in FIGS. 16 and 17, spinal implant system 10, similar to the systems and methods described herein, comprises a surgical instrument 140, similar to instrument 40, described above. Surgical instrument 140 includes arms 140a, 140b, similar to arms 40a, 40b, described herein. Arm 140a extends between an end 142a and an end 144a. End 142a includes an extender 146 configured for engagement with SAS 14 at vertebra L4, similar to that described herein. End 144a includes a flat configuration having a surface 148a that defines a channel 150a. Arm 140b extends between an end 142b and an end 144b. End 142a includes an extender 146 configured for engagement with SAS 14 at vertebra L5, similar to that described herein. End 144b includes a flat configuration having a surface 148b that defines a channel 150b. Channels 150a, 150b are configured for movable disposal of a bolt 152, which is configured to facilitate relative rotation of arms 140a, 140b. In some embodiments, bolt 152 includes a lock for fixing relative position of arms 140a, 140b.

A wedge 156 is disposed between arms 140a, 140b. Wedge 156 includes an end 158 and an end 159 and is tapered between ends 158, 159 to cause expansion and/or contraction of arms 140a, 140b as wedge 90 translates, in the direction shown by arrows G, between arms 140a, 140b. Wedge 156 is configured to translate laterally between arms 140a, 140b to adjust and increase and/or decrease an apex of arms 140a, 140b and the distance from vertebrae L4, L5 to increase/decrease lordosis.

Wedge 156 is attached to an actuator 162 to translate wedge 156, in the direction shown by arrows G. Actuator 162 includes a handle 164 and a longitudinal member, such as, for example, a cork screw tether 102. In some embodiments, as actuator 162 is rotated, tether 102 is wound about handle 164 such that wedge 156 is drawn and translated posteriorly with tether 102 causing wedge 156 to translate laterally between arms 140a, 140b. As such, arms 140a, 140b are caused to relatively rotate. In some embodiments, handle 164 is connected with a threaded shaft and wedge 156 includes an inner threaded surface that defines a cavity for disposal of the threaded shaft. As actuator 162 is rotated, the threaded shaft rotates in engagement with wedge 156 such that wedge 156 is translated posteriorly or anteriorly relative to the threaded shaft causing wedge 156 to translate laterally between arms 140a, 140b to relatively rotate arms 140a, 140b.

Surgical instrument 140, as shown in FIGS. 16 and 17, is employed to manipulate vertebrae L4. L5. Arms 140a, 140b are attached with SAS 14, via extenders 146, to manipulate vertebrae L4, L5. As actuator 162 is rotated, tether 102 is wound about handle 164 such that wedge 156 is drawn and translated posteriorly with tether 102 causing wedge 156 to translate laterally between arms 140a, 140b, as described herein. As such, arms 140a, 140b are caused to relatively rotate such that endplate surfaces E1, E2 adjacent posterior portion P exert a compressive force, in the direction shown by arrows E in FIG. 17, on cage 12 such that cage 12 comprises a posterior fulcrum during posterior compression. Arms 140a, 140b selectively rotate vertebrae L4, L5, in the direction shown by arrows F in FIG. 17, about cage 12 to achieve segmental lordosis of vertebrae L4, L5. In some embodiments, as shown in FIG. 17, surgical instrument 140 includes a protractor 160, similar to protractor 60 described herein, connected via bolt 152.

In some embodiments, spinal implant system 10 as depicted generally in FIGS. 14-17, may be used in a direct lateral (DLIF) procedure. Referring generally to FIGS. 14 and 16, surgical instruments 40 and/or 140 may be used in pairs to tether both sides of the vertebrae as cage 12 (for example, using two pairs of SAS 14 across a pair of vertebrae). In such embodiments, cage 12 may comprise a large-footprint DLIF cage, such as, for example, the CLYDESDALE® spinal system available from Medtronic Spinal and Biologics. In some such cases, the DLIF cage 12 may be used as a fulcrum about which the instruments 40 and/or 140, depending on the embodiment, may impart lordosis-inducing forces as described throughout the present disclosure. In DLIF embodiments, the cage 12 may be placed more anteriorly than the cage 12 depicted generally in FIGS. 14-15. For example, in some DLIF cases, the patient may be placed in a lateral position such that posterior access to the instruments 40 and/or 140 may be available to the surgeon, along with simultaneous DLIF access for the insertion of the cage 12. In some such DLIF cases, the cage 12 may be placed in an anterior half of the disc space between vertebrae and the pairs of instruments 40 and/or 140 may be used to impart bilateral lordosis-inducing forces across the fulcrum established by the cage 12.

In one embodiment, as shown in FIGS. 18 and 19, spinal implant system 10, similar to the systems and methods described herein, comprises a surgical instrument, such as, for example, a distractor 170. Distractor 170 is utilized for transverse disc dissection and preparation across a posterior portion of a vertebral space, as described herein. Distractor 170 includes an arm 172 and a transverse arm 174. Arm 174 is disposed at an angle α, as shown in FIG. 18, relative to arm 172. In some embodiments, angle α is disposed in a range 0 through 180 degrees. In some embodiments, angle α is 90 degrees.

Arm 172 includes a handle 176 configured to facilitate manipulation of distractor 170. In some embodiments, arm 172 includes markings 178 configured to indicate a depth of distractor 170 within a vertebral space to prevent insertion of distractor 170 in a spinal canal and/or prevent insertion outside the annulus pulpous of vertebral space S.

In some embodiments, arm 174 includes a cutting end 180. Cutting end 180 includes a cupped portion 182 and a ring curette 184. Cutting end 180 is disposed at an angle β, as shown in FIG. 19, relative to arm 174 and relative to an axis disposed transverse to arm 172. In some embodiments, angle β is disposed in a range 0 through 180 degrees. In some embodiments, angle β is 30 degrees. Curette 184 is configured as a right-angled down-biting ring to facilitate safe disc removal transversely across a posterior portion of a vertebral space, as described herein. In some embodiments, cutting end 180 is configured to facilitate ventrally pushing tissue within a vertebral space into an anterior portion of the vertebral space for safe removal of the tissue. In some embodiments, cutting end 180 separates cartilaginous endplate material and the separated fragments are pushed anteriorly into a center portion of the vertebral space. The fragments are removed by ronguers (not shown).

Figure 22:
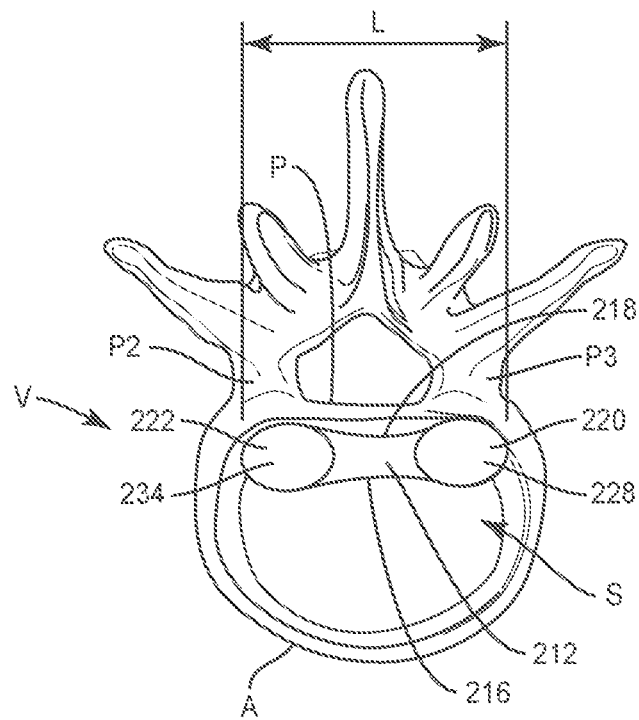
FIG. 22 is a plan view of components of one embodiment of a system in accordance with the principles of the present disclosure disposed with vertebrae.
Figure 23:
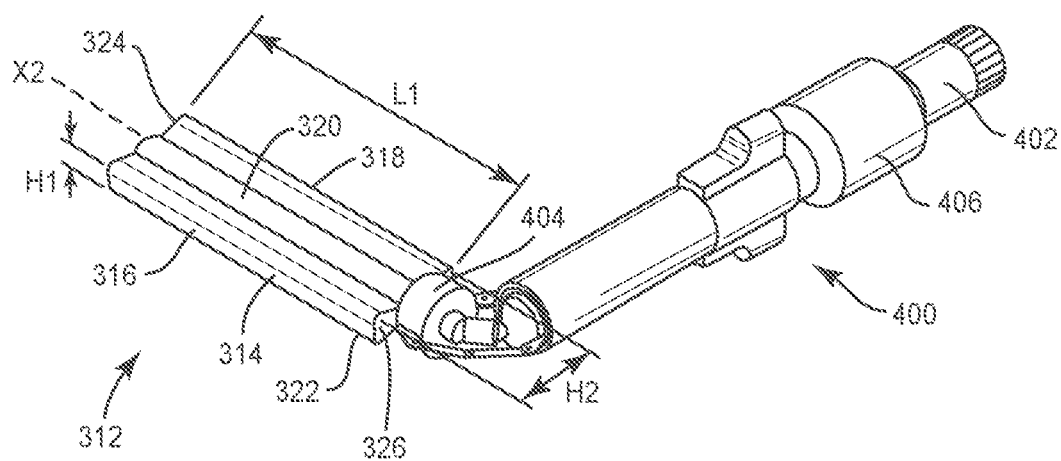
FIG. 23 is a perspective view of components of one embodiment of a system in accordance with the principles of the present disclosure.
Figure 24:
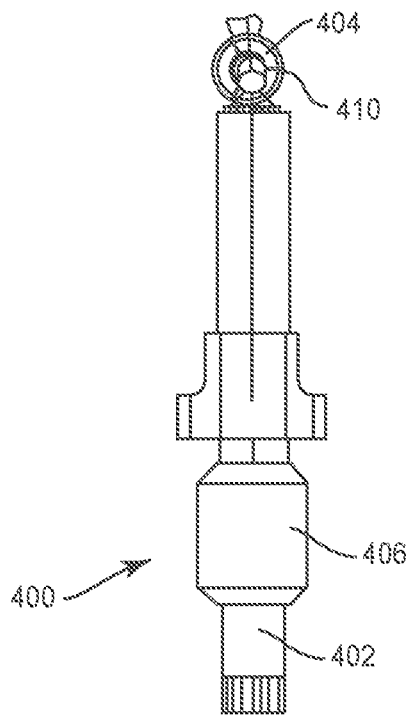
FIG. 24 is a side view of the components shown in FIG. 23.
Figure 25:
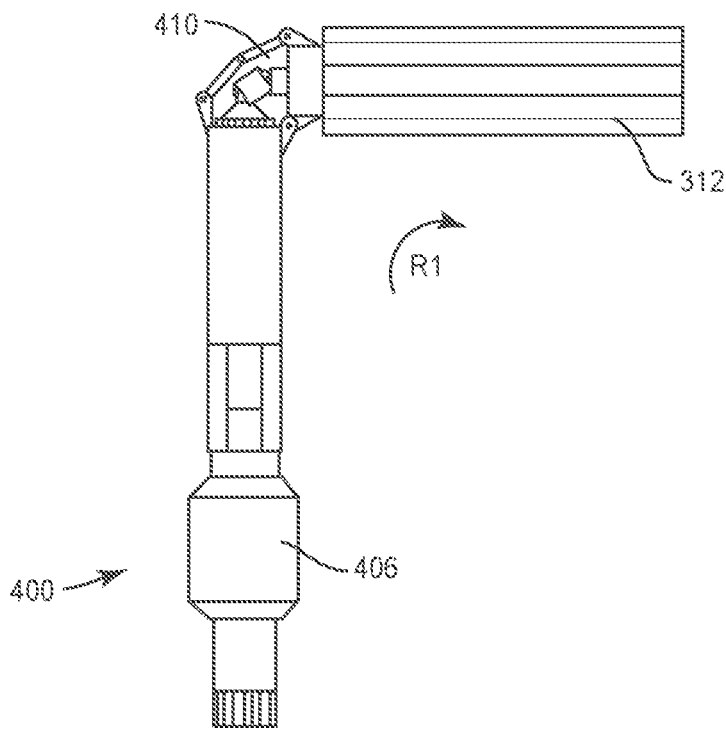
FIG. 25 is a side view of the components shown in FIG. 23.
Figure 26:
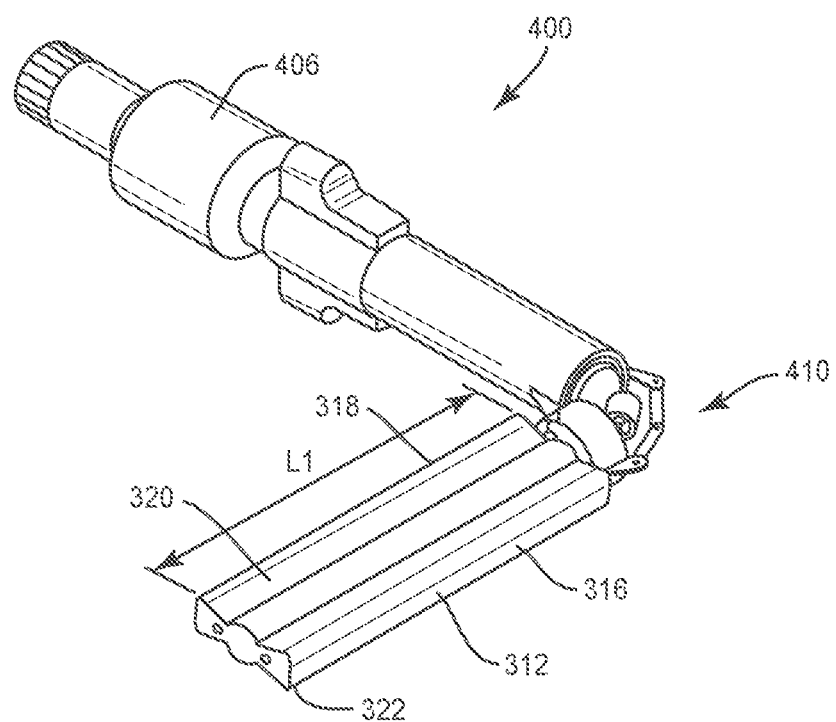
FIG. 26 is a perspective view of the components shown in FIG. 23.

In one embodiment, as shown in FIGS. 20-22, spinal implant system 10, similar to the systems and methods described herein, comprises a cage 212, similar to cage 12, described herein. Cage 212 defines an axis X1. Cage 212 includes a body 214 that extends between an anterior oriented surface 216 and a posterior oriented surface 218. In some embodiments, upon disposal of cage 212 with vertebrae V, anterior surface 216 is oriented to face an anterior side of a body, such as, for example, an anterior portion A of vertebral space S of vertebrae V. In some embodiments, upon disposal of cage 212 with vertebrae V, posterior surface 218 is oriented to face a posterior side of the body and be disposed adjacent a posterior portion of vertebrae, such as, for example, a posterior portion P of vertebral space S of vertebrae V. In some embodiments, cage 212 is configured as a stabilizing implant that provides a fixed fulcrum for restoring lordosis and height to selected vertebrae V. Cage 212 is configured to rotate about axis X1 for disposal transversely within vertebral space 5, as described herein.

Body 214 extends between an end 220 and an end 222 and defines a length L and a height H. Length L is configured to span between a lateral margin of a pedicle P2 and a lateral margin of an oppositely disposed pedicle P3. In some embodiments, height H is less than length L. In some embodiments, height H is 8 to 10 mm. Height H of cage 212 facilitates disc height restoration at posterior portion P of vertebral space S between vertebrae L4, L5.

End 220 includes an extension 226 that defines a vertebral engaging surface 228 and a vertebral engaging surface 230. Surfaces 228, 230 are each configured to engage tissue of a vertebral body. In some embodiments, surface 228 and/or surface 230 may be rough, textured, porous, semi-porous, dimpled, knurled, toothed, grooved and/or polished to facilitate engagement with tissue. In some embodiments, the vertebral tissue may include intervertebral tissue, endplate surfaces and/or cortical bone.

End 222 includes an extension 232 that defines a vertebral engaging surface 234 and a vertebral engaging surface 236. Surfaces 234, 236 are each configured to engage tissue of a vertebral body. In some embodiments, surface 234 and/or surface 236 may be rough, textured, porous, semi-porous, dimpled, knurled, toothed, grooved and/or polished to facilitate engagement with tissue. In some embodiments, the vertebral tissue may include intervertebral tissue, endplate surfaces and/or cortical bone.

In some embodiments, cage 212 is configured for insertion via a TLIF procedure, similar to that described herein. Cage 212 is inserted into vertebral space S along length L. As cage 212 enters vertebral space S, cage 212 is rotated about axis X1 for disposal transversely across vertebral space S at posterior portion P for selective orientation of cage 212 with vertebrae L4, L5 to align cage 212 with posterior portion P of the vertebral endplates having a higher strength and resistance to subsidence. Cage 212 is disposed such that end 220 is disposed adjacent pedicle P3 and end 222 is disposed adjacent pedicle P2. Surfaces 228, 234 engage an endplate surface of vertebra L4. Surfaces 230, 236 engage an endplate surface of vertebra L5. Cage 212 comprises a posterior fulcrum during posterior compression upon manipulation of vertebrae L4, L5 to selectively rotate vertebrae L4, L5 about cage 212 to achieve segmental lordosis of vertebrae L4, L5, as described herein. In some embodiments, bone graft and/or other biologics can be inserted anteriorly into vertebral space S prior to insertion of cage 212.

Figure 27:
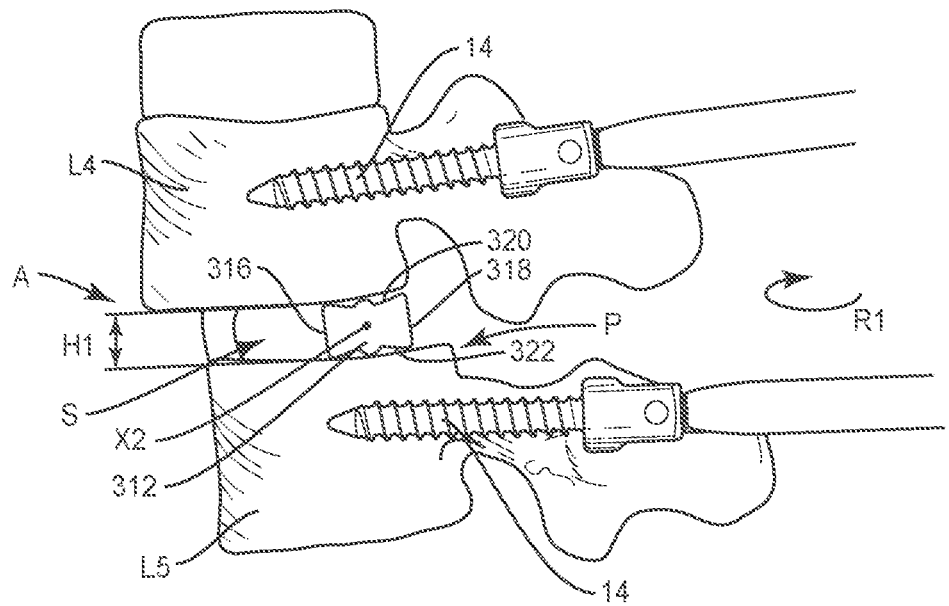
FIG. 27 is a break away side view of components of one embodiment of a system in accordance with the principles of the present disclosure disposed with vertebrae.
Figure 28:
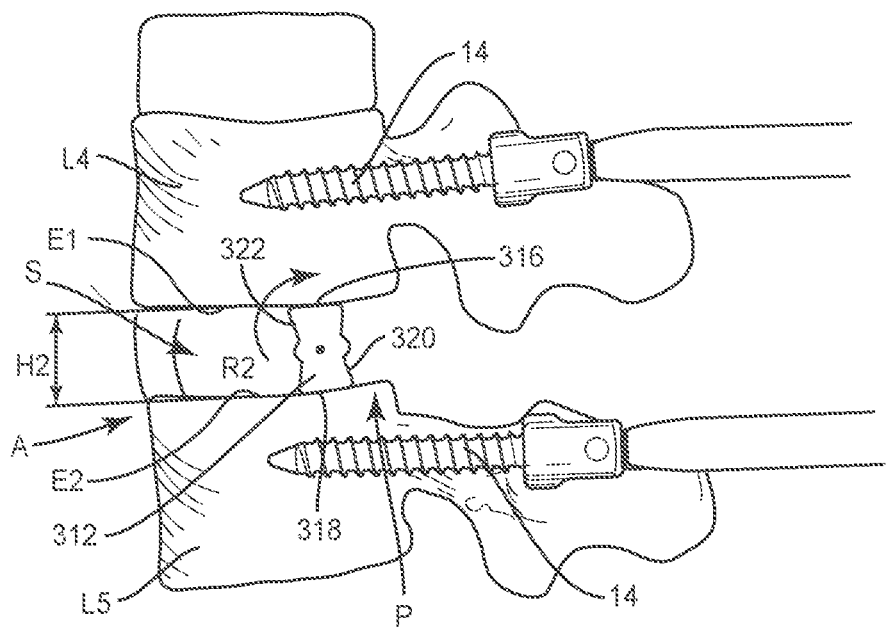
FIG. 28 is a side view of the components and vertebrae shown in FIG. 27.

In one embodiment, as shown in FIGS. 23-28, spinal implant system 10, similar to the systems and methods described herein, comprises an interbody implant 312, similar to the spinal implants described herein. Interbody implant 312 defines an axis X2. Interbody implant 312 includes a body 314 having surfaces 316, 318, 320 and 322. In some embodiments, surfaces 316, 318, 320 and 322 form an I-beam configuration. Interbody implant 312 is configured as a stabilizing implant that provides a fixed fulcrum for restoring lordosis and height to selected vertebrae L4, L5, as shown in FIGS. 27 and 28. In some embodiments, interbody implant 312 is configured to rotate about axis X2 for disposal transversely within the disc space, as described herein.

Body 314 extends between an end 324 and an end 326. Body 314 defines a length L1 and a height H1. Length L1 is configured to span across a lateral margin of a pedicle and a lateral margin of an oppositely disposed pedicle adjacent posterior portion P. Body 314 includes a height H2. In some embodiments, height H1 and height H2 are less than length L1. Rotation between height H1 and height H2 facilitates disc height restoration at posterior portion P.

Upon rotation of interbody implant 312, as described herein, surfaces 316, 318 define vertebral engaging surfaces. Surfaces 316, 318 are each configured to engage tissue of the endplate surface of vertebrae L4, L5. In some embodiments, surface 316 and/or surface 318 may be rough, textured, porous, semi-porous, dimpled, knurled, toothed, grooved and/or polished to facilitate engagement with tissue. In some embodiments, the vertebral tissue may include intervertebral tissue, endplate surfaces and/or cortical bone.

In some embodiments, interbody implant 312 is configured for insertion via a TLIF procedure, similar to that described herein. A surgical instrument, such as, for example, an inserter 400 is utilized to insert interbody implant 312 and rotate interbody implant 312, as described herein. Inserter 400 is a dynamic insertion instrument such that inserter 400 enables insertion of interbody implant 312 into vertebral space S in a selected configuration, such as, for example, along a linear pathway, straight ahead orientation and/or rotation. After insertion and/or disposal of interbody implant 312 at a surgical site, inserter 400 is configured to initially rotate and angle interbody implant 312, as shown by arrow R1 in FIGS. 25 and 27, transversely between the pedicles. Inserter 400 is configured to achieve a second rotation to rotate interbody implant 312 about axis X2, as shown by arrow R2 in FIG. 28, between height H1 and height H2 for engagement with endplate surfaces E1, E2 and to facilitate reduction of the spondylolisthesis.

Inserter 400 extends between and end 402 and an end 404. End 402 includes an actuator 406 configured to actuate insertion and rotation of interbody implant 312. End 404 is configured for releasable attachment with interbody implant 312. Inserter 400 includes a planetary gear-train 410 configured to provide an increased mechanical advantage and facilitate orientation and alignment of interbody implant 312 during insertion, first rotation R1 and second rotation R2. In some embodiments, planetary gear train 410 is a mechanism for transmitting rotational motion by spur or bevel gears that include planet gears or pinions that undergo compound motion and have a moving axis of rotation. In some embodiments, a carrier supports the axles of the planet gears. In some embodiments, the planet gears mesh with a central gear that rotate about the shaft of the mechanism.

Interbody implant 312 is inserted into vertebral space S along length L such that surface 320 engages vertebra L4 and surface 322 engages vertebra L5. As shown in FIG. 22, as interbody implant 312 enters vertebral space S, inserter 400 is actuated to rotate interbody implant 312, as shown by arrow R1 in FIGS. 25 and 27, for orientation of interbody implant 312 transversely across vertebral space S at posterior portion P between pedicles, as described herein. Interbody implant 312 is rotated for disposal with vertebrae L4, L5 to align interbody implant 212 with posterior portion P and the vertebral endplate surfaces having a higher strength and resistance to subsidence. Inserter 400 is actuated for rotation R2 of interbody implant 312, as shown in FIG. 28, such that surface 316 rotates into engagement with endplate surface E1 of vertebra L4 and surface 318 rotates into engagement with endplate surface E2 of vertebra L5, such that surfaces E1, E2 exert a compressive force on interbody implant 312. Rotation R2 increases the height of cage 312 from height H1 to height H2 such that interbody implant 312 comprises a fulcrum for rotation of vertebrae L4, L5 about interbody implant 312 to facilitate creating segmental lordosis. In some embodiments, cage 312 comprises a posterior fulcrum during posterior compression upon manipulation of vertebrae L4, L5 to selectively rotate vertebrae L4, L5 about cage 312 to achieve segmental lordosis of vertebrae L4, L5, as described herein. In some embodiments, bone graft and/or other biologics can be inserted anteriorly into vertebral space S prior to insertion of cage 312.

Figure 29:
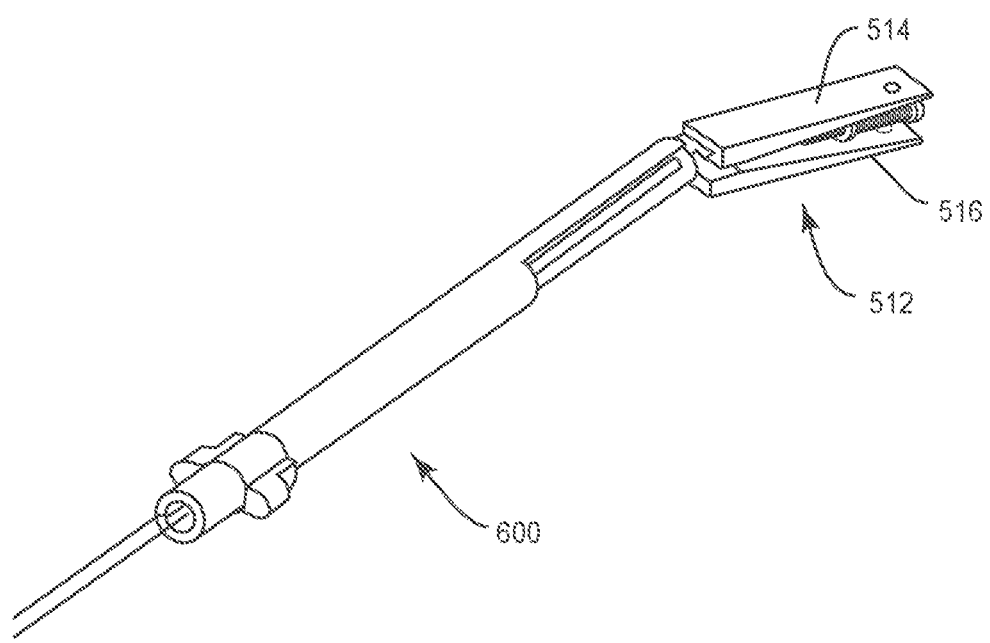
FIG. 29 is a perspective view of components of one embodiment of a system in accordance with the principles of the present disclosure.
Figure 30:
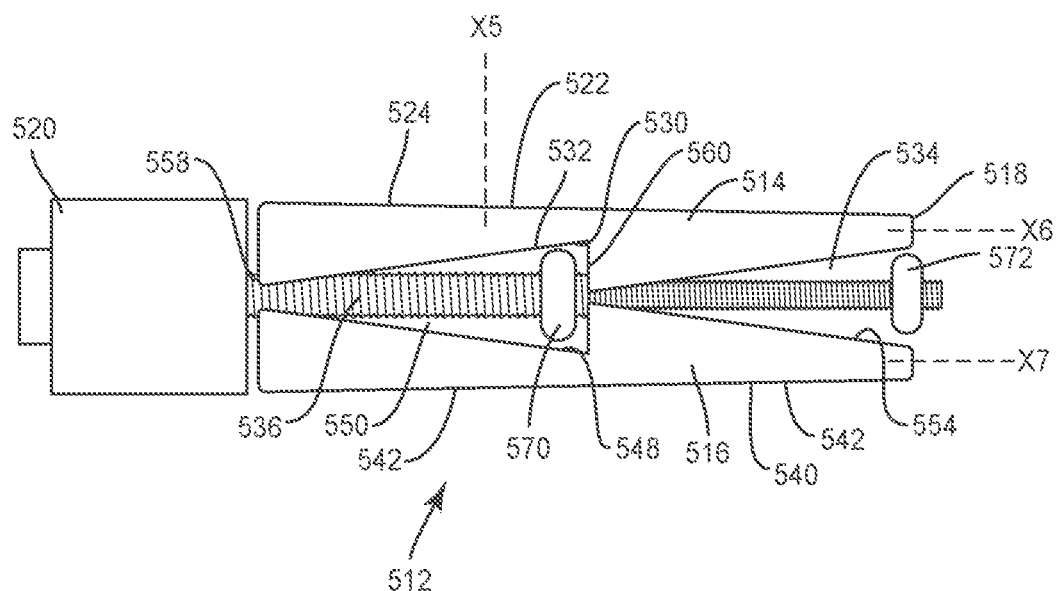
FIG. 30 is a side view of components of one embodiment of a system in accordance with the principles of the present disclosure.
Figure 31:
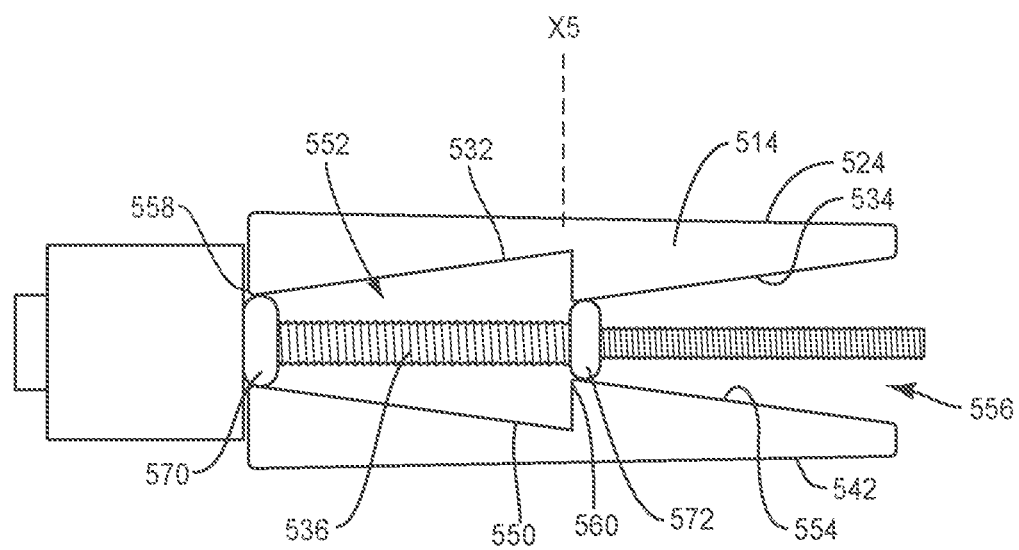
FIG. 31 is a side view of the components shown in FIG. 30.

In one embodiment, as shown in FIGS. 29-31, spinal implant system 10, similar to the systems and methods described herein, comprises a cage 512, similar to the spinal implants described herein. Cage 512 includes a member 514 and a member 516. Cage 512 defines an axis X5 and extends between an end 518 and an end 520. Member 514 defines a longitudinal axis X6 disposed substantially perpendicular to axis X5. Member 514 includes a surface 522 that defines a vertebral engaging surface 524.

Member 514 includes a surface 530 that defines a tapered cavity 532 and a tapered cavity 534. Cavities 532, 534 are configured for moveable disposal of an actuator, such, as for example, a screw 536, as described herein. Member 516 defines a longitudinal axis X7 disposed substantially perpendicular to axis X5 and parallel to axis X6. Member 516 includes a surface 540 that defines a vertebral engaging surface 542.

Member 516 includes a surface 548 that defines a tapered cavity 550 in communication with cavity 532 to form an opening 552. Member 516 includes a tapered cavity 554 in communication with cavity 534 to form an opening 556. Opening 552 includes a stop 558 configured to limit relative movement of members 514, 516. Openings 552, 556 are in communication at a stop 560 configured to limit relative movement of members 514, 516. Openings 552, 556 are configured for disposal of screw 536, as described herein. Members 514, 516 are configured for relative translation upon actuation of screw 536.

Screw 536 is configured for disposal with openings 552, 556. Screw 536 includes a wedge 570 and a wedge 572. Wedges 570, 572 each include an inner threaded surface that defines a cavity for disposal of screw 536. As screw 536 is rotated, screw 536 rotates in engagement with wedges 570, 572 such that wedges 570, 572 are translated relative to screw 536 causing wedges 570, 572 to translate laterally and expand members 514, 516. Wedges 570, 572 translate along screw 536 causing members 514, 516 to expand and increase in height along axis X5 for engagement with vertebrae L4, L5 forming a posterior fulcrum during posterior compression to selectively rotate vertebrae L4, L5 about cage 512 to achieve segmental lordosis of vertebrae L4, L5, as described herein.

Screw 536 extends parallel to axes X6, X7. Screw 536 is configured to rotate within openings 552, 556 to facilitate expansion and contraction of members 514, 516 via wedges 570, 572. Rotation of screw 536 causes axial translation of wedges 570, 572 such that wedges 570, 572 are movable relative to members 514, 516 along the tapered cavities 532, 550, 534, 554 of openings 552, 556 to expand and collapse cage 512 to increase and/or decrease lordosis about cage 512.

An instrument 600 is connected with cage 512 to facilitate insertion of cage 512 and rotation of cage 512 for positioning transversely between pedicles. Cage 512 is inserted into a vertebral space (not shown) such that surface 524 engages an endplate surface of a vertebra and surface 542 engages an endplate surface of an adjacent vertebra. As cage 512 enters the vertebral space, instrument 600 is actuated to dispose cage 512 transversely across a posterior portion of the vertebral space, similar to that described herein, for selective orientation of cage 512 with vertebrae to align cage 512 with the posterior portion of vertebral endplate surfaces having a higher strength and resistance to subsidence.

Instrument 600 is configured to actuate screw 536 to cause expansion and/or contraction of cage 512 at the posterior portion forming a posterior fulcrum during posterior compression to selectively rotate the vertebrae about cage 512 to achieve segmental lordosis of the vertebrae, as described herein.

Figure 32:
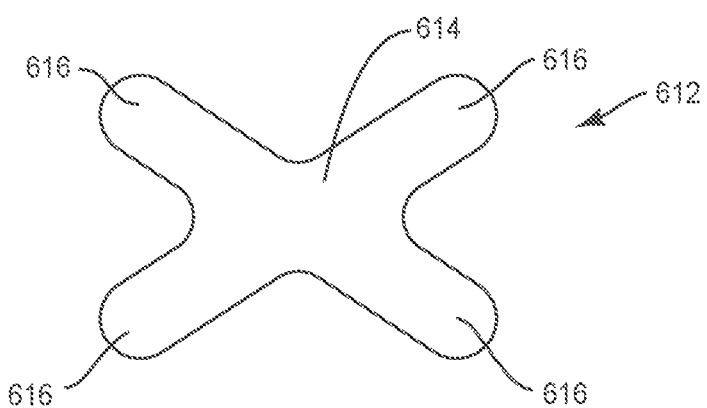
FIG. 32 is a side view of components of one embodiment of a system in accordance with the principles of the present disclosure.

In one embodiment, as shown in FIG. 32, spinal implant system 10, similar to the systems and methods described herein, comprises a cage 612, similar to the spinal implants described herein. Cage 612 includes a cloverleaf configuration having a central portion 614 with extensions 616. Cage 612 loads endplate surfaces adjacent a posterior portion of vertebrae adjacent to pedicles, similar to that described herein, to decrease the risk of subsidence into tissue.

Figure 33:
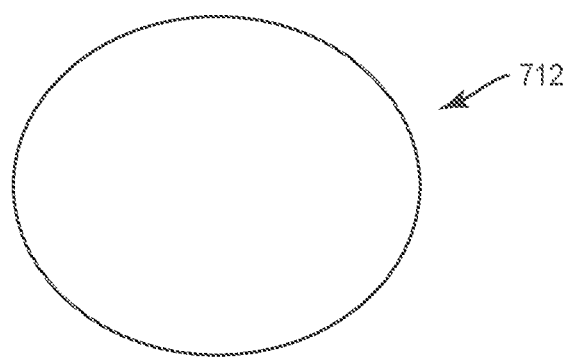
FIG. 33 is a side view of components of one embodiment of a system in accordance with the principles of the present disclosure.

In one embodiment, as shown in FIG. 33, spinal implant system 10, similar to the systems and methods described herein, comprises a cage 712, similar to the spinal implants described herein. Cage 712 includes an oval configuration and loads endplate surfaces adjacent a posterior portion of vertebrae adjacent to pedicles, similar to that described herein, to decrease the risk of subsidence into tissue.

Figure 34:
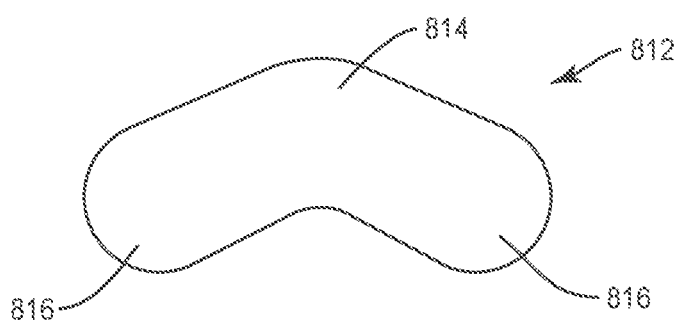
FIG. 34 is a side view of components of one embodiment of a system in accordance with the principles of the present disclosure.

In one embodiment, as shown in FIG. 34, spinal implant system 10, similar to the systems and methods described herein, comprises a cage 812, similar to the spinal implants described herein. Cage 812 includes an arcuate configuration and loads endplate surfaces adjacent a posterior portion of vertebrae adjacent to pedicles, similar to that described herein, to decrease the risk of subsidence into tissue.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A surgical system comprising:
 a spinal implant comprising a body including a first vertebral engaging surface and a second vertebral engaging surface being disposable adjacent a posterior portion of an intervertebral disc space;
 bone graft disposable within the intervertebral disc space; and
 a surgical instrument to compress tissue with the spinal implant such that one or more vertebra rotate about the spinal implant, the surgical instrument including a cork screw tether.

2. A surgical system as recited in claim 1, wherein the surgical instrument includes extenders connected with the cork screw tether.

3. A surgical system as recited in claim 1, wherein the cork screw tether includes extenders and a movable wedge disposed therebetween.

4. A surgical system as recited in claim 1, wherein the spinal implant includes a clover-leaf configuration that is configured to engage tissue adjacent the posterior portion.

5. A surgical system as recited in claim 1, wherein the spinal implant includes a dumbbell configuration that is configured to be inserted adjacent the posterior portion in a vertical access direction with a TLIF approach.

6. A surgical system as recited in claim 1, wherein the spinal implant includes a posteriorly expanding cage.

7. A surgical system as recited in claim 1, further comprising first and second screws, the surgical instrument comprising a first extender that is coupled to the first screw and a second extender that is coupled to the second screw, the screws being configured to be attached with vertebrae such that the extenders can selectively rotate the vertebrae.

8. A surgical system as recited in claim 7, further comprising a wedge disposed between the extenders and an actuator including a handle and the cork screw tether, the handle being configured to be rotated to wind the cork screw tether about the handle and translate the wedge laterally between the extenders to cause the extenders to rotate.

9. A surgical system comprising:
 an interbody implant disposable within an intervertebral disc space;
 bone graft disposable within the intervertebral disc space; and
 a surgical instrument configured to compress tissue with the interbody implant such that one or more vertebra rotate about the interbody implant, the surgical instrument including an actuator, the actuator including a handle, a cork screw tether and a wedge, the handle being configured to be rotated to wind the cork screw tether about the handle and translate the wedge.

10. A surgical system as recited in claim 9, wherein the surgical instrument includes extenders connected with the cork screw tether.

11. A surgical system as recited in claim 9, wherein the cork screw tether includes extenders, the wedge being disposed between the extenders.

12. A surgical system as recited in claim 9, wherein the interbody implant includes a clover-leaf configuration.

13. A surgical system as recited in claim 9, wherein the interbody implant includes a dumbbell configuration.

14. A surgical system as recited in claim 9, wherein the interbody implant includes a posteriorly expanding cage.

15. A surgical system as recited in claim 9, further comprising first and second screws, the surgical instrument comprising a first extender that is coupled to the first screw and a second extender that is coupled to the second screw, the screws being configured to be attached with vertebrae such that the extenders can selectively rotate the vertebrae.

16. A surgical system comprising:
 a spinal implant; and
 a surgical instrument including a cork screw tether, the surgical instrument being configured to compress tissue with the spinal implant such that one or more vertebra rotate about the spinal implant.

17. A surgical system as recited in claim 16, further comprising first and second screws, the surgical instrument comprising a first extender that is coupled to the first screw and a second extender that is coupled to the second screw, the screws being configured to be attached with vertebrae such that the extenders can selectively rotate the vertebrae.

18. A surgical system as recited in claim 16, wherein the surgical instrument comprises an actuator, the actuator including a handle, a wedge and the cork screw tether, the handle being configured to be rotated to wind the cork screw tether about the handle and translate the wedge.

19. A surgical system as recited in claim 16, wherein the surgical instrument includes extenders connected with the cork screw tether.

20. A surgical system as recited in claim 16, wherein the cork screw tether includes extenders and a wedge, the wedge being disposed between the extenders.

* * * * *